United States Patent
Kodama et al.

(10) Patent No.: US 6,509,329 B1
(45) Date of Patent: *Jan. 21, 2003

(54) CYCLIC DIAMINE COMPOUND WITH 6-MEMBERED RING GROUPS

(75) Inventors: Tatsuhiko Kodama, Tokio (JP); Masahiro Tamura, Higashimurayama (JP); Toshiaki Oda, Higashimurayama (JP); Yukiyoshi Yamazaki, Higashimurayama (JP); Masahiro Nishikawa, Higashimurayama (JP); Takeshi Doi, Higashimurayama (JP); Yoshinori Kyotani, Higashiyamato (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,697

(22) Filed: Jun. 29, 2001

(51) Int. Cl.$^7$ .................... C07D 251/12; C07D 243/08; C07D 241/04; C07D 295/18; A61K 31/495

(52) U.S. Cl. ............................ 514/212.01; 514/217.03; 514/217.04; 514/217.05; 514/217.06; 514/252.12; 514/252.13; 514/252.14; 540/575; 544/295; 544/357; 544/360; 544/392

(58) Field of Search .................................. 544/295, 357, 544/360, 392; 540/575; 514/212.01, 217.03, 217.04, 217.05, 217.06, 252.12, 252.13, 252.14

(56) References Cited

U.S. PATENT DOCUMENTS 6,340,682 B1 * 1/2002 Ishiwata et al. ......... 514/235.8

FOREIGN PATENT DOCUMENTS

| JP | 9-143075 | 6/1997 |
| JP | 10-67656 | 3/1998 |
| JP | 10-147568 | 6/1998 |
| JP | 10-182550 | 7/1998 |
| JP | 11-92382 | 4/1999 |
| JP | 2000-86641 | 3/2000 |
| JP | 2000-509070 | 7/2000 |
| JP | 2000-319277 | 11/2000 |

OTHER PUBLICATIONS

Y. Ohkawara, et al., "In Situ Expression of the Cell Adhesion Molecules in Bronchial Tissues Form Asthmatics with Air Flow Limitation: In Vivo Evidence of VCAM–1/VLA–4 Interaction in Selective Eosinophil Infiltration", *American Journal of Respiratory Cell and Molecular Biology*, 1995, vol. 12, pp. 4–12.

A. Sakai, et al., "P–Selectin and Vascular Cell Adhesion Molecule–1 are Focally Expressed in Aortas of Hypercholesterolemic Rabbits Before Intimal Accumulation of Macrophages and T Lymphocytes", *Arteriosclerosis, Thrombosis, and Vascular Biology*, Feb. 1997, vol. 17, No. 2, pp. 310–316.

H. Wakita, et al., "E–Selectin and Vascular Cell Adhesion Molecule–1 as Critical Adhesion Molecules for Infiltration of T Lymphocytes and Eosinophils in Atopic Dermatitis", *Journal of Cutaneous Pathology*, 1994, pp. 33–39.

T. Satoh, et al., "Cyclophosphamide–Induced Blood and Tissue Eosinophilia in Contact Sensitivity: Mechanism of Hapten–Induced Eosinophil Recruitment into the Skin", *European Journal of Immunology*, 1997, vol. 27, pp. 85–91.

P. P. Tak, et al., "Expression of Adhesion Molecules in Early Rheumatoid Synovial Tissue", *Clinical Immunology and Immunopathology*, Dec. 1995, vol. 77, No. 3, pp. 236–242.

S. Albelda, et al., "Adhesion Molecules and Inflammatory Injury", *The FASEB Journal*, Reviews, May 1994, vol. 8, pp. 504–512.

T. A. Springer, "Traffic Signals on Endothelium for Lymphocyte Recirculation and Leukocyte Emigration", *Annu. Rev. Physiol.*, 1995, vol. 57, pp. 827–872.

S. A. Michie, et al., "The Roles of α4–Integrins in the Development of Insulin–=Dependent Diabetes Mellitus", *Curr. Top. Microbiol. Immunol.*, 1998, vol. 231, pp. 65–83.

N. Ebihara, et al., "Anti VLA–4 Monoclonal Antibody Inhibits Eosinophil Infiltration in Allergic Conjunctivitis Model of Guinea Pig", *Current Eye Research*, 1999, vol. 19, No. 1, pp. 20–25.

(List continued on next page.)

*Primary Examiner*—Bruck Kifle
(74) *Attorney, Agent, or Firm*—Oblon, Spivak, McClelland, Maier & Neustadt, P.C.

(57) ABSTRACT

A cyclic diamine compound of formula (1):

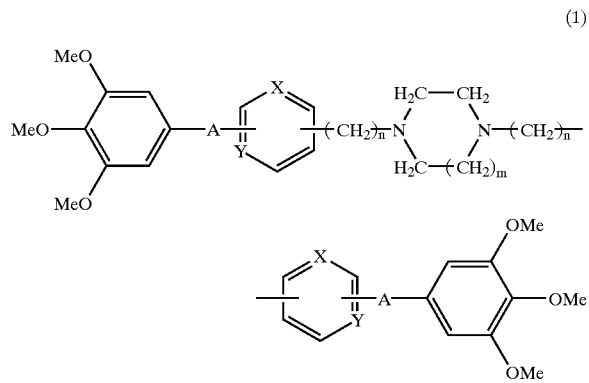

wherein A is a single bond or C≡C; X and Y are individually CH or a nitrogen atom; m is 1 or 2; and n is a number of 1 to 5; an acid-addition salt thereof, or a hydrate thereof. The compound has excellent inhibitory effects on both cell adhesion and cell infiltration and is useful as a medicine for prevention or treatment of diseases such as allergy, asthma, rheumatism, arteriosclerosis and inflammation.

17 Claims, No Drawings

OTHER PUBLICATIONS

S. M. Whitcup, et al., "Blocking ICAM–1 (CD54) and LFA–1 (CD11a) Inhibits Experimental Allergic Conjunctivitis", *Clinical Immunology*, Nov. 1999, vol. 93, No. 2, pp. 107–113.

A. Soriano, et al., "VCAM–1, but not ICAM–1 or MAd-CAM–1, Immunoblockade Ameliorates DSS–Induced Colitis in Mice", *Laboratory Investigation*, Oct. 2000, vol. 80, No. 10, pp. 1541–1551.

A. Zeidler, et al., "Therapeutic Effects of Antibodies Against Adhesion Molecules in Murine Collagen Type II–Induced Arthritis", *Autoimmunity*, 1995, vol. 21, pp. 245–252.

F. Bendjelloul, et al., "Intercellular Adhesion Molecule–1 (ICAM–1) Deficiency Protects Mice Against Severe Forms of Experimentally Induced Colitis", *Clinical and Experimental Immunology*, 2000, vol. 119, pp. 57–63.

W. W. Wolyniec, et al., "Reduction of Antigen–Induced Airway Hyperreactivity and Eosinophilia in ICAM–1–Deficient Mice", *American Journal of Respiratory Cell and Molecular Biology*, 1998, vol. 18, pp. 777–785.

D. C. Bullard, et al., "Reduced Susceptibility to Collagen–Induced Arthritis in Mice Deficient in Intercellular Adhesion Molecule–$1^1$", *The Journal of Immunology*, 1996, vol. 157, pp. 3153–3158.

D. H. Boschelli, et al., "Inhibition of E–Selectin–, ICAM–1–, and VCAM–1–Mediated Cell Adhesion by Benzo[b]Thiophene–, Benzofuran–, Indole–, and Naphthalene–2–Carboxamides: Identification of PD 144795 as an Antiinflammatory Agent", *Journal of Medicinal Chemistry*, 1995, vol. 38, No. 22, pp. 4597–4614.

\* cited by examiner

CYCLIC DIAMINE COMPOUND WITH 6-MEMBERED RING GROUPS

BACKGROUND OF THE INVENTION

1. Field of the Invention

The present invention relates to novel cyclic diamine compounds which have inhibitory effects on both cell adhesion and cell infiltration and are useful as anti-asthmatic agents, anti-allergic agents, anti-rheumatic agents, anti-arteriosclerotic agents, anti-inflammatory agents or the like, and medicines containing such compounds.

2. Description of the Background Art

In various inflammatory diseases, infiltration of leukocytes into inflammatory sites is observed. For example, infiltration of eosinophils into the bronchus in asthma (Ohkawara, Y. et al., Am.. J. Respir. Cell Mol. Biol., 12, 4–12 (1995)), infiltration of macrophages and T lymphocytes into the aorta in arteriosclerosis (Sakai, A. et al., Arterioscler Thromb. Vasc. Biol., 17, 310–316 (1997)), infiltration of T lymphocytes and eosinophils into the skin in atopic dermatitis (Wakita H. et al, J. Cutan. Pathol., 21, 33–39 (1994)) or contact dermatitis (Satoh, T. et al., Eur. J. Immunol., 27, 85–91 (1997)), and infiltration of various leukocytes into rheumatoid synovial tissue (Tak, PP. et al., Clin. Immunol. Immunopathol., 77, 236–242 (1995)), have been reported.

Infiltration of these leukocytes is elicited by cytokines, chemokines, lipids, and complements produced in inflammatory sites (Albelda, S M. et al., FASEB J., 8, 504–512 (1994)). Activated leukocytes adhere to vascular endothelial cells through an interaction called rolling or tethering with endothelial cells activated likewise. Thereafter, the leukocytes transmigrate through endothelium to infiltrate into the inflammatory sites (Springer, T A., Annu. Rev. Physiol., 57, 827–872 (1995)). In adhesion of leukocytes to the vascular endothelial cells in this process, various cell adhesion molecules such as an immunoglobulin superfamily (ICAM-1, VCAM-1 and the like), a selectin family (E-selectin and the like), an integrin family (LFA-1, VLA-4 and the like) and CD44, which are induced on the surfaces of the cells by stimulation by cytokines or the like, play important roles ("Rinsho Meneki (Clinical Immune)", 30, Supple. 18 (1998)), and relationship between the disorder state and aberrant expression of the cell adhesion molecules is noted.

Accordingly, an agent capable of inhibiting cell adhesion can be useful as an agent for preventing and treating allergic diseases such as bronchial asthma, dermatitis, rhinitis and conjunctivitis; autoimmune diseases such as rheumatoid arthritis, nephritis, inflammatory bowel diseases, diabetes and arteriosclerosis; and chronic inflammatory diseases. In fact, it has been reported that antibodies against adhesion molecules on leukocytes such as LFA-1, Mac-1 and VLA-4 or antibodies against ICAM-1, VCAM-1, P-selectin, E-selectin and the like on vascular endothelial cells, which become ligands thereof, inhibit infiltration of leukocytes into inflammatory sites in animal models. For example, neutralizing antibodies against VCAM-1 and VLA-4, which is a counter receptor thereof, can delay development of diabetes in an NOD mouse model which spontaneously causes the diabetes (Michie, S A. et al., Curr. Top. Microbiol. Immunol., 231, 65–83 (1998)). It has also been reported that an antibody against VLA-4 or ICAM-1 and its counter receptor, LFA-1, inhibits infiltration of eosinophils in a guinea pig and mouse allergic conjunctivitis model (Ebihara et al., Current Eye Res., 19, 20–25 (1999); Whitcup, S M et al., Clin. Immunol., 93, 107–113 (1999)), and a monoclonal antibody against VCAM-1 inhibits infiltration of leukocytes in a mouse DSS-induced colitis model to attenuate colitis (Soriano, A. et al., Lab. Invest., 80, 1541–1551 (2000)). Further, an anti-VLA-4 antibody and an anti-CD44 antibody reduce the incidence of disease symptoms in a mouse collagen arthritis model (Zeidler, A. et al., Autoimmunity, 21, 245–252 (1995)). Even in cell adhesion molecule deficient-mice, inhibition of infiltration of leukocytes into inflammatory tissues is observed, likewise in inflammatory models (Bendjelloul, F. et al., Clin. Exp. Immunol., 119, 57–63 (2000); Wolyniec, W W. et al., Am. J. Respir. Cell Mol. Biol., 18, 777–785 (1998); Bullard, D C. et al., J. Immunol., 157, 3153–3158 (1996)).

However, it is difficult to develop antibody-based drugs because they are polypeptides and so oral administration is a problem. Moreover, the possible side effects due to antigenicity and allergic reactions are problems.

On the other hand, there have been various investigations of low-molecular weight compounds having an inhibitory effect on cell adhesion with a view toward permitting oral administration. These compounds include benzothiophene derivatives (Boschelli, DH. et al., J. Med. Chem., 38, 4597–4614 (1995)), naphthalene derivatives (Japanese Patent Application Laid-Open No. 10-147568), hydroxybenzoic acid derivatives (Japanese Patent Application Laid-Open No. 10-182550), lignans (Japanese Patent Application Laid-Open No. 10-67656), 2-substituted benzothiazole derivatives (Japanese Patent Application Laid-Open No. 2000-086641 through PCT route, condensed pyrazine compounds (Japanese Patent Application Laid-Open No. 2000-319277 through PCT route), 2,6-dialkyl-4-silylphenol (Japanese Patent Application Laid-Open Re-Publication No. 2000-509070 through PCT route) and the like. However, the goal has not often been sufficiently achieved under the circumstances. Cyclic diamine compounds described in Japanese Patent Application Laid-Open Nos. 9-143075 and 11-92382 do not exhibit a sufficient inhibitory effect on cell adhesion, and so there is a demand for further improvement in activity.

SUMMARY OF THE INVENTION

An object of the present invention is to provide a substance having inhibitory effects on both cell adhesion and cell infiltration, plus excellent anti-asthmatic effects, anti-allergic effects, anti-rheumatic effects, anti-arteriosclerotic effects and anti-inflammatory effects.

With the foregoing circumstances in mind, the present inventors carried out an extensive investigation to find a substance which inhibits cell adhesion and cell infiltration. As a result, we found that compounds represented by the general formula (1), have excellent cell adhesion-inhibiting effects and cell infiltration-inhibiting effects and are useful as anti-allergic agents, anti-asthmatic agents, anti-rheumatic agents, anti-arteriosclerotic agents or anti-inflammatory agents.

The present invention provides a cyclic diamine compound represented by the following general formula (1):

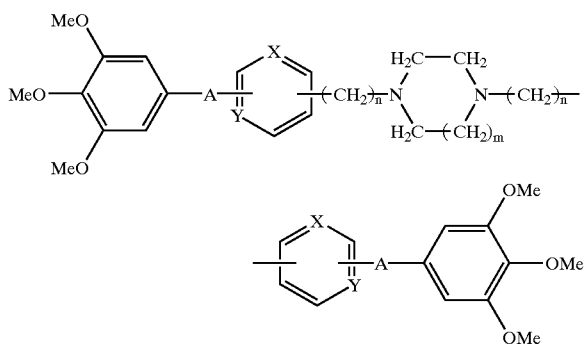

(1)

wherein A is a single bond or C≡C; X and Y are individually CH or a nitrogen atom; m is 1 or 2; and n is a number of 1 to 5;
an acid-addition salt thereof, or a hydrate thereof.

According to the present invention, there is also provided a medicine comprising the above cyclic diamine compound, an acid-addition salt thereof, or a hydrate thereof as an active ingredient.

According to the present invention, there is further provided a medicinal composition comprising the above cyclic diamine compound, the acid-addition salt thereof, or the hydrate thereof and a pharmaceutically acceptable carrier.

According to the present invention, there is still further provided a method for treating a disease caused by cell adhesion and/or cell infiltration, which comprises administering an effective amount of the above cyclic diamine compound, an acid-addition salt thereof, or a hydrate thereof to a patient who requires such treatment.

DETAILED DESCRIPTION OF THE PREFERRED EMBODIMENTS

In the general formula (1), A is a single bond or C≡C, and X and Y are individually CH or a nitrogen atom. Accordingly, the ring containing X and Y is a benzene, pyridine or pyrimidine ring. The value of m is 1 or 2; n is a number from 1 to 5, with a number of 1 to 3 being preferred.

No particular limitation is imposed on the acid-addition salts of the compounds (1) according to the invention as long as they are pharmaceutically acceptable salts. Examples include the acid-addition salts of mineral acids, such as hydrochlorides, hydrobromides, hydriodides, sulfates and phosphates; and acid-addition salts of organic acids, such as benzoates, methanesulfonates, ethanesulfonates, benzenesulfonates, p-toluenesulfonates, oxalates, maleates, fumarates, tartrates, citrates and acetates.

The compounds of formula (1) according to the present invention may be present in the form of solvates typified by hydrates, and the solvates are embraced in the present invention.

The compounds (1) can be prepared in accordance with, for example, the following reaction formula:

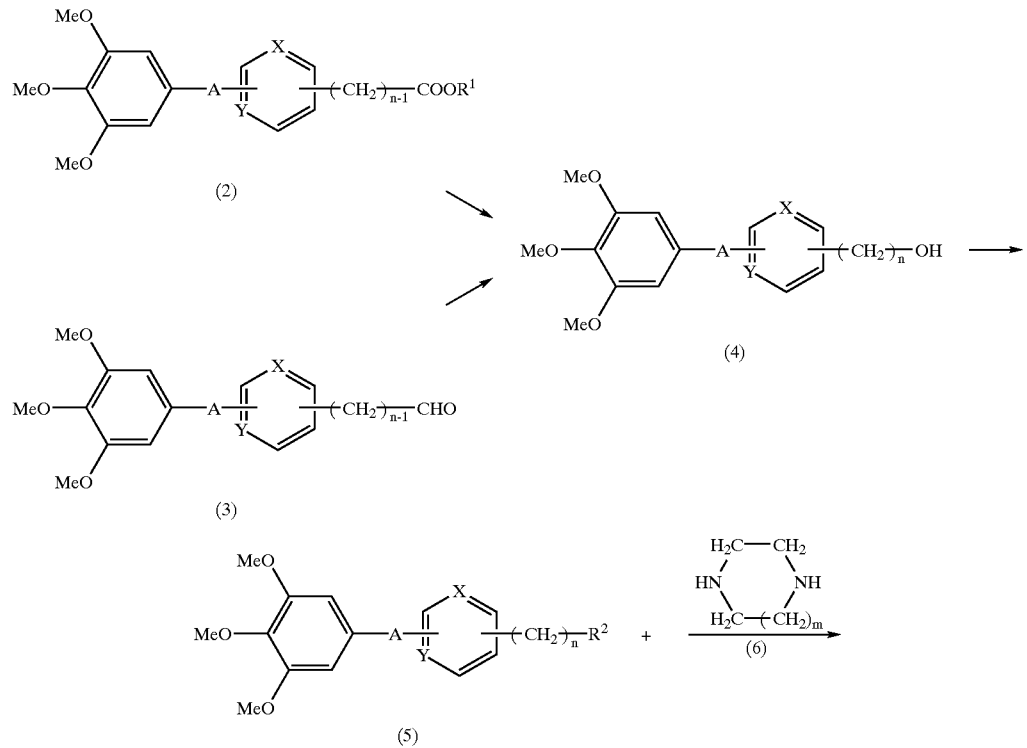

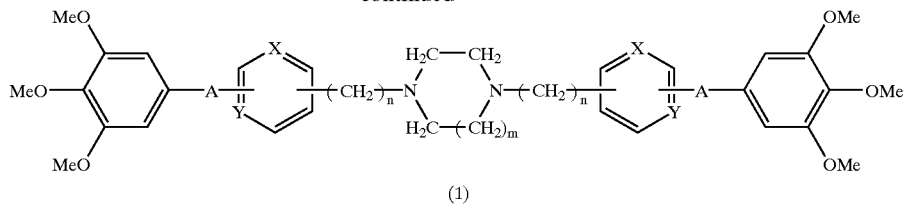

(1)

wherein $R^1$ is a hydrogen atom or lower alkyl group, $R^2$ is a halogen atom, or an alkylsulfonyloxy or arylsulfonyloxy group, and A, X, Y, m and n have the same meaning as defined above.

More specifically, the compounds of formula (1) are obtained by reducing a carboxy derivative (2) or an aldehyde (3) to obtain an alcohol (4), reacting this alcohol with a halogenating agent or sulfonylating agent to produce a compound (5) and condensing the compound (5) with a cyclic diamine.

Examples of the halogen atom represented by $R^2$ include chlorine and bromine atoms. Alkylsulfonyloxy groups include the methanesulfonyloxy group, and arylsulfonyloxy groups include the p-toluenesulfonyloxy group.

The reduction reaction of the carboxy derivative (2) or the aldehyde (3) is preferably conducted by, for example, causing the carboxy derivative (2) or the aldehyde (3) to react at −20° C. to room temperature, preferably 0° C. to room temperature for several seconds to several hours, preferably 30 minutes using a reducing agent such as lithium aluminum hydride in tetrahydrofuran (THF).

The halogenating agent used in the halogenation of the age alcohol (4) includes thionyl chloride. On the other hand, as the alkylsulfonylating agent, methanesolfonyl chloride or the like is used, and as the arylsulfonating agent, p-tolutenesulfonyl chloride or the like is used. The halogenation or sulfonyloxylation of the alcohol (4) is preferably conducted by stirring the reactants at −20° C. to room temperature, preferably 0° C. to room temperature for 1 hour to several days, preferably 5 hours in a solvent such as chloroform, dichloromethane, ethyl acetate, ether, THF or dioxane for thionyl chloride, or in the presence of a base such as triethylamine or pyridine in a solvent such as chloroform, dichloromethane, ethyl acetate, ether, THF, dioxane or pyridine for methanesulfonyl chloride or the like.

The condensation reaction of the compound (5) with the cyclic diamine is conducted by, for example, stirring the reactants at room temperature to 100° C., preferably 50° C. for 1 hour to several days, preferably 5 hours in the presence of a base such as potassium carbonate in a solvent such as N,N-dimethylformamide (DMF), dimethyl sulfoxide (DMSO) or acetonitrile.

The compounds (1) according to the present invention are obtained by the above-described process and may further be purified by using an ordinary purification means such as recrystallization or column chromatography as needed. Also as needed, the compounds may be converted into the desired salts or solvates by methods known in the art.

The compounds (1) according to the present invention, or acid-addition salts or solvates thereof thus obtained have excellent inhibitory effects on cell adhesion as demonstrated in the Examples, which will be described subsequently, and are useful as medicines for treatment or prevention of diseases of animals including humans, such as asthma, allergy, rheumatism, arteriosclerosis and inflammation.

The medicine according to the present invention comprises a compound (1), a salt thereof, or a solvate thereof as an active ingredient. The form of administration may be suitably selected as necessary for the therapeutic application intended without any particular limitation, including oral preparations, injections, suppositories, ointments, inhalants, eye drops, nose drops and plasters. A composition suitable for use in these administration forms can be prepared by blending a pharmaceutically acceptable carrier in accordance with the conventional preparation method publicly known by those skilled in the art.

When an oral solid preparation is formulated, an excipient, and optionally, a binder, a disintegrator, a lubricant, a colorant, a taste corrigent, a smell corrigent and the like are added to the compound (1), and the resulting composition can be formulated into tablets, coated tablets, granules, powders, capsules, etc. in accordance with methods known in the art. As such additives described above, any additives may be used which are generally used in the pharmaceutical field. Examples include excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dry starch, sodium alginate, agar powder, sodium hydrogencarbonate, calcium carbonate, sodium lauryl sulfate, monoglyceryl stearate and lactose; lubricants such as purified talc, stearic acid salts, borax and polyethylene glycol; and taste corrigents such as sucrose, orange peel, citric acid and tartaric acid.

When an oral liquid preparation is formulated, a taste corrigent, buffer, stabilizer, smell corrigent and/or the like are added to compound (1), and the resulting composition can be formulated into internal liquid preparations, syrup preparations, elixirs, etc. in accordance with methods known in the art. In this case, vanillin as the taste corrigent, may be used. As the buffer, sodium citrate may be mentioned. As examples of the stabilizer, tragacanth, gum arabic and gelatin may be mentioned.

When an injection is formulated, a pH adjustor, buffer, stabilizer, isotonicity agent, local anesthetic and the like may be added to compound (1) according to the present invention, and the resultant composition can be formulated into subcutaneous, intramuscular and intravenous injections in accordance with methods known in the art. Examples of the pH adjustor and buffer in this case include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the isotonicity agent include sodium chloride and glucose.

When a suppository is formulated, a carrier preparation known in the art, for example, polyethylene glycol, lanoline, cacao butter, fatty acid triglyceride or the like, and optionally, a surfactant such as Tween (trade mark) and the like are added to the compound (1), and the resultant composition can be formulated into suppositories in accordance with methods known in the art.

When an ointment is formulated, a base material, stabilizer, wetting agent, preservative and the like, which are generally used, are blended with compound (1) as needed, and the resulting blend is mixed and formulated into ointments in accordance with methods known. Examples of the base material include liquid paraffin, white vaseline, bleached beeswax, octyldodecyl alcohol and paraffin. Examples of the preservative include methyl p-hydroxybenzoate, ethyl p-hydroxybenzoate and propyl p-hydroxybenzoate.

Besides the above preparations, inhalants, eye drops and nose drops may also be formulated in accordance with known methods known in the art.

The dose of the medicine according to the present invention varies according to the age, weight and condition of the patient to be treated, the administration method, the number of times of administration, and the like. It is however preferred that the medicine is generally orally or parenterally administered at once or in several portions in a dose of 1 to 1,000 mg per day in terms of compound (1), for an adult.

The present invention will hereinafter be described in more detail by the following Examples. However, the invention is not limited to these examples.

PREPARATION EXAMPLE 1

Synthesis of Ethyl 2-(3,4,5-trimethoxyphenyl) benzoate 3,4,5-Trimethoxyphenylboronic acid (639 mg) and ethyl 2-bromobenzoate (479 mg) were suspended in a mixed solvent of toluene (20 mL) and THF (15 mL), and to the suspension 2M sodium carbonate (6 mL) and tetrakis (triphenylphosphine) palladium(0) (175 mg) were added. The mixture was stirred overnight at 90° C. under an argon atmosphere. Ethyl acetate was added to the reaction mixture to separate an organic layer. The organic layer was washed with saturated brine, dried over anhydrous sodium magnesium and concentrated under reduced pressure. The residue was purified by column chromatography on silica gel (hexane:ethyl acetate=5:1) to obtain the title compound.

Yield: 655 mg (69%). $^1$H-NMR (400 MHz, CDCl$_3$) δ: 1.04 (t, 3H, J=7.2 Hz), 3.86 (s, 6H), 3.89 (s, 3H), 4.12 (q, 2H, J=7.2 Hz), 6.54 (s, 2H), 7.40–7.42 (m, 2H), 7.51 (t, 1H, J=7.8 Hz), 7.77 (d, 1H, J=6.8 Hz).

PREPARATION EXAMPLE 2

Synthesis of 2-(3,4,5-Trimethoxyphenyl)benzyl Alcohol

Ethyl 2-(3,4,5-trimethoxyphenyl)benzoate (655 mg) was dissolved in THF (20 mL), and to the solution lithium aluminum hydride (80 mg) was added at 0° C. under an argon atmosphere. The mixture was stirred at 0° C. for 1 hour as it is. A small amount of water and then sodium sulfate were added to the reaction mixture, and the reaction mixture was filtered through celite. The filtrate was concentrated under reduced pressure, and the resultant crude crystals were recrystallized from ethyl acetate-hexane to obtain the title compound.

Yield: 630 mg (theoretical amount). $^1$H-NMR (400 MHz, CDCl$_3$) δ: 3.85 (s, 6H), 3.90 (s, 3H), 4.61 (s, 2H), 6.61 (s, 2H), 7.26–7.39 (m, 3H), 7.53 (d, 1H, J=6.8 Hz).

PREPARATION EXAMPLE 3

Synthesis of 2-(3,4,5-Trimethoxyphenyl)benzyl Chloride 2-(3,4,5-Trimethoxyphenyl)benzyl alcohol (630 mg) was dissolved in chloroform (10 mL), and to the solution thionyl chloride (0.153 mL) was added at 0° C. After 30 minutes, the mixture was warmed to room temperature and stirred for 4 hours. The reaction mixture was washed with water and saturated brine, dried over anhydrous sodium sulfate and concentrated under reduced pressure. The residue was then recrystallized from chloroform-hexane to obtain the title compound.

Yield: 615 mg (theoretical amount). $^1$H-NMR (400 MHz, CDCl$_3$) δ: 3.87 (s, 6H), 3.90 (s, 3H), 4.53 (s, 2H), 6.66 (s, 2H), 7.29–7.32 (m, 1H), 7.34–7.39 (m, 2H), 7.50–7.52 (m, 1H).

EXAMPLE 1

Synthesis of N,N'-bis[2-(3,4,5-Trimethoxyphenyl) benzyl]-piperazine Dihydrochloride

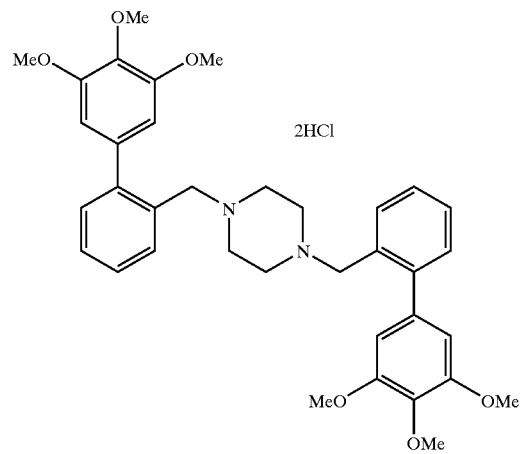

2-(3,4,5-Trimethoxyphenyl)benzyl chloride (298 mg) and piperazine (43 mg) were dissolved in DMF (5 mL), and to the solution potassium carbonate (138 mg) was added. The mixture was stirred at 80° C. for 4 hours and concentrated under reduced pressure. Water was added to the residue to conduct extraction with chloroform. The resultant organic layer was washed with saturated brine, dried over anhydrous magnesium sulfate and then concentrated under reduced pressure. The residue was purified by column chromatography on silica gel (chloroform:methanol=40:1) to obtain a free base of the title compound. This compound was dissolved in ethyl acetate, and to the solution an ethyl acetate solution of 4 M hydrogen chloride was added to provide a dihydrochloride.

Yield: 238 mg (74%). $^1$H-NMR (400 MHz, DMSO-d$_6$, 120° C.) δ: 2.95 (br, 8H), 3.77 (s, 6H), 3.80 (s, 12H), 3.99 (s, 4H), 6.59 (s, 4H), 7.28–7.30 (m, 2H), 7.37–7.42 (m, 4H), 7.80 (d, 2H, J=6.3 Hz). m/z (EI): 598 [M$^+$].

EXAMPLE 2

Synthesis of N,N'-bis[2-(3,4,5-Trimethoxyphenyl)benzyl]-homopiperazine Dihydrochloride

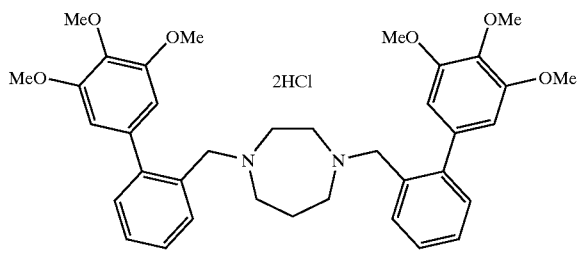

2-(3,4,5-Trimethoxyphenyl)benzyl chloride (307 mg) and homopiperazine (53 mg) were reacted in the same manner as in Example 1 to obtain a free base of the title compound. This compound was converted into a dihydrochloride in the same manner as in Example 1.

Yield: 181 mg (51%). $^1$H-NMR (400 MHz, DMSO-d$_6$, 120° C.) δ: 2.20 (br, 2H), 3.11 (br, 4H), 10 3.39 (br, 4H), 3.77 (s, 6H), 3.81 (s, 12H), 4.20 (s, 4H), 6.58 (s, 4H), 7.29–7.31 (m, 2H), 7.39–7.44 (m, 4H), 7.99 (d, 2H, J=7.8 Hz). m/z (EI): 612 [M$^+$].

PREPARATION EXAMPLE 4

Synthesis of Ethyl 3-(3,4,5-Trimethoxyphenyl)benzoate 3,4,5-Trimethoxyphenylboronic acid (3.7 g) and ethyl 3-bromobenzoate (4.02 g) were reacted in the same manner as in Preparation Example 1 to obtain the title compound.

Yield: 5.09 g (92%). $^1$H-NMR (400 MHz, CDCl$_3$) δ: 1.42 (t, 3H, J=7.1 Hz), 3.90 (s, 3H), 3.94 (s, 6H), 4.41 (q, 2H, J=7.1 Hz), 6.79 (s, 2H), 7.50 (t, 1H, J=7.8 Hz), 7.73(dt, 1H, J=7.1 Hz, 1.5 Hz), 8.01(dt, 1H, J=7.8 Hz, 1.4 Hz), 8.23 (t, 1H, J=1.8 Hz).

PREPARATION EXAMPLE 5

Synthesis of 3-(3,4,5-Trimethoxyphenyl)benzyl Alcohol

Ethyl 3-(3,4,5-trimethoxyphenyl)benzoate (5.09 g) was treated in the same manner as in Preparation Example 2 to obtain the title compound.

Yield: 4.25 g (97%). $^1$H-NMR (400 MHz, CDCl$_3$) δ: 1.87 (t, 1H, J=6.0 Hz), 3.89 (s, 3H), 3.92 (s, 6H), 4.76 (d, 1H, J=5.6 Hz), 6.77 (s, 2H), 7.34 (d, 1H, J=7.4 Hz), 7.42 (t, 1H, J=7.5 Hz), 7.48 (d, 1H, J=7.6 Hz), 7.55 (s, 1H).

Preparation Example 6

Synthesis of 3-(3,4,5-Trimethoxyphenyl)benzyl Chloride 3-(3,4,5-Trimethoxyphenyl)benzyl alcohol (1.21 g) was treated in the same manner as in Preparation Example 3 to obtain the title compound.

Yield: 893 mg (69.2%). $^1$H-NMR (400 MHz, CDCl$_3$) δ: 3.87 (s, 3H), 3.90 (s, 6H), 4.62 (s, 2H), 6.75 (s, 2H), 7.33 (d, 1H, J=7.6 Hz), 7.39 (t, 1H, J=7.7 Hz), 7.48 (d, 1H, J=7.6 Hz), 7.54 (s, 1H).

EXAMPLE 3

Synthesis of N,N'-bis[3-(3,4,5-Trimethoxyphenyl)benzyl]-piperazine

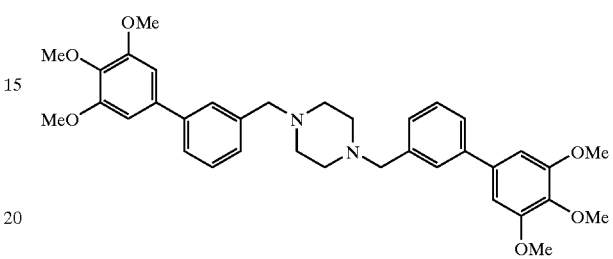

3-(3,4,5-Trimethoxyphenyl)benzyl chloride (120 mg) and piperazine (17 mg) were reacted in the same manner as in Example 1 to obtain the title compound as a free base.

Yield: 78 mg (65%). $^1$H-NMR (400 MHz, CDCl$_3$) δ: 2.55 (br, 8H), 3.58 (s, 4H), 3.88 (s, 6H), 3.92 (s, 12H), 6.77 (s, 4H), 7.30 (d, 2H, J=7.6 Hz), 7.36 (t, 2H, J=7.5 Hz), 7.43 (d, 2H, J=7.6 Hz), 7.48 (br, 2H). m/z (EI): 671 [M$^+$].

EXAMPLE 4

Synthesis of N,N'-bis[3-(3,4,5-Trimethoxyphenyl)benzyl]-homopiperazine

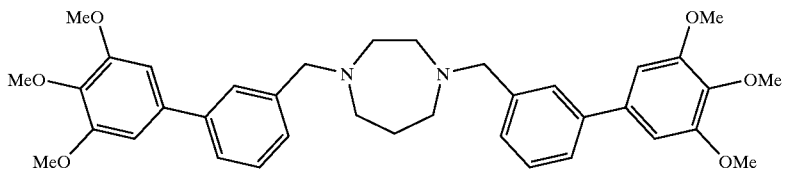

3-(3,4,5-Trimethoxyphenyl)benzyl chloride (184 mg) and homopiperazine (52 mg) were reacted in the same manner as in Example 1 to obtain the title compound as a free base.

Yield: 159 mg (87%). $^1$H-NMR (400 MHz, CDCl$_3$) δ: 1.89–1.92 (m, 2H), 2.80–2.86 (m, 8H), 3.76 (s, 4H), 3.89 (s, 6H), 3.92 (s, 12H), 6.79 (s, 4H), 7.31–7.45 (m, 6H), 7.57 (s, 2H). m/z (EI): 685 [M$^+$].

PREPARATION EXAMPLE 7

Synthesis of Ethyl 4-(3,4,5-Trimethoxyphenyl)benzoate 3,4,5-Trimethoxyphenylboronic acid (2.01 g) and ethyl 4-bromobenzoate (2.29 g) were reacted in the same manner as in Preparation Example 1 to obtain the title compound.

Yield: 2.99 g (95%). $^1$H-NMR (400 MHz, CDCl$_3$) δ: 1.42 (t, 3H, J=7.2 Hz), 3.90 (s, 3H), 3.94 (s, 6H), 4.38 (q, 2H, J=7.2 Hz), 6.81 (s, 2H), 7.62 (d, 2H, J=8.2 Hz), 8.10 (d, 2H, J=8.2 Hz).

PREPARATION EXAMPLE 8

Synthesis of 4-(3,4,5-Trimethoxyphenyl)benzyl Alcohol

Ethyl 4-(3,4,5-Trimethoxyphenyl)benzoate (2.99 g) was treated in the same manner as in Preparation Example 2 to obtain the title compound.

Yield: 1.83 g (71%).

PREPARATION EXAMPLE 9

Synthesis of 4-(3,4,5-Trimethoxyphenyl)benzyl chloride:

4-(3,4,5-Trimethoxyphenyl)benzyl alcohol (1.83 g) was treated in the same manner as in Preparation Example 3 to obtain the title compound.

Yield: 1.65 g (84%). $^1$H-NMR (400 MHz, CDCl$_3$) δ: 3.90 (s, 3H), 3.93 (s, 6H), 4.65 (s, 2H), 6.77 (s, 2H), 7.46 (d, 2H, J=8.0 Hz), 7.55 (d, 2H, J=8.0 Hz).

EXAMPLE 5

Synthesis of N,N'-bis[4-(3,4,5-Trimethoxyphenyl)benzyl]-piperazine Dimethanesulfonate:

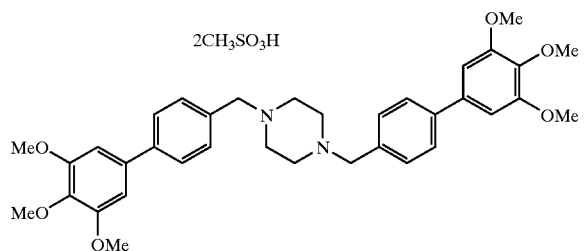

4-(3,4,5-Trimethoxyphenyl)benzyl chloride (442 mg) and piperazine (65 mg) were reacted in the same manner as in Example 1 to obtain a free base of the title compound. This compound was dissolved in methanol, and to the solution methanesulfonic acid was added to obtain the title compound.

Yield: 360 mg (61%). $^1$H-NMR (400 MHz, DMSO-d$_6$, 120° C.) δ: 2.49 (s, 6H), 3.21 (s, 8H), 3.75 (s, 6H), 3.87 (s, 12H), 4.17 (s, 4H), 6.91 (s, 4H), 7.53 (d, 4H, J=8.2 Hz), 7.68 (d, 4H, J=8.2 Hz). m/z (EI): 598 [M$^+$].

EXAMPLE 6

Synthesis of N,N'-bis[4-(3,4,5-Trimethoxyphenyl)benzyl]-homopiperazine Dimaleate:

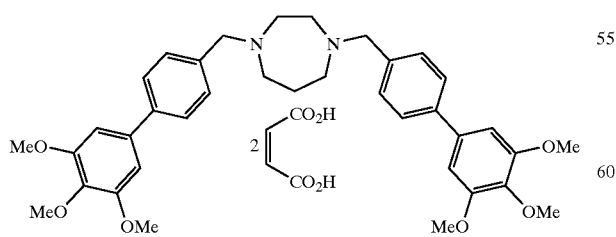

4-(3,4,5-Trimethoxyphenyl)benzyl chloride (35 mg) and homopiperazine (83 mg) were reacted in the same manner as in Example 1 to obtain a free base of the title compound. This compound was dissolved in methanol, and to the solution methanesulfonic acid was added to obtain the title compound.

Yield: 224 mg (32%). $^1$H-NMR (400 MHz, DMSO-d$_6$, 120° C.) δ: $^{2.00-2.06}$ (m, 2H), 3.10 (t, 4H, J=5.7 Hz), 3.14 (s, 4H), 3.76 (s, 6H), 3.88 (s, 12H), 4.08 (s, 4H), 6.13 (s, 4H), 6.91 (s, 4H), 7.49 (d, 4H, J=8.2 Hz), 7.67 (d, 4H, J=8.2 Hz). m/z (EI): 612 [M$^+$].

PREPARATION EXAMPLE 10

Synthesis of Ethyl 2-(3,4,5-Trimethoxyphenyl)nicotinate 3,4,5-Trimethoxyphenylboronic acid (694 mg) and ethyl 2-chloronicotinate (608 mg) were reacted in the same manner as in Preparation Example 1 to obtain the title compound.

Yield: 799 mg (77%). $^1$H-NMR (400 MHz, CDCl$_3$) δ: 1.10 (t, 3H, J=7.2 Hz), 3.89 (s, 9H), 4.19 (q, 2H, J=7.2 Hz), 6.79 (s, 2H), 7.34(dd, 1H, J=7.8 Hz, 4.8 Hz), 8.06(dd, 1H, J=7.8 Hz, 1.7 Hz), 8.75(dd, 1H, J=4.8 Hz, 1.7 Hz).

PREPARATION EXAMPLE 11

Synthesis of 3-Hydroxymethyl-2-(3,4,5-trimethoxyphenyl)-pyridine

Ethyl 2-(3,4,5-trimethoxyphenyl)nicotinate (468 mg) was treated in the same manner as in Preparation Example 2 to obtain the title compound.

Yield: 293 mg (72%). $^1$H-NMR (400 MHz, CDCl$_3$) δ: 3.90 (s, 9H), 4.72 (s, 2H), 6.83 (s, 2H), 7.32(dd, 1H, J=7.9 Hz, 4.8 Hz), 7.92(dd, 1H, J=7.9 Hz, 1.7 Hz), 8.62(dd, 1H, J=4.8 Hz, 1.7 Hz).

PREPARATION EXAMPLE 12

Synthesis of 3-Chloromethyl-2-(3,4,5-trimethoxyphenyl)-pyridine

3-Hydroxymethyl-2-(3,4,5-trimethoxyphenyl)pyridine (293 mg) was treated in the same manner as in Preparation Example 3 to obtain the title compound.

Yield: 311 mg (theoretical amount).

EXAMPLE 7

Synthesis of N,N'-bis[ [2-(3,4,5-Trimethoxyphenyl)pyridin-3-yl]methyl]piperazine

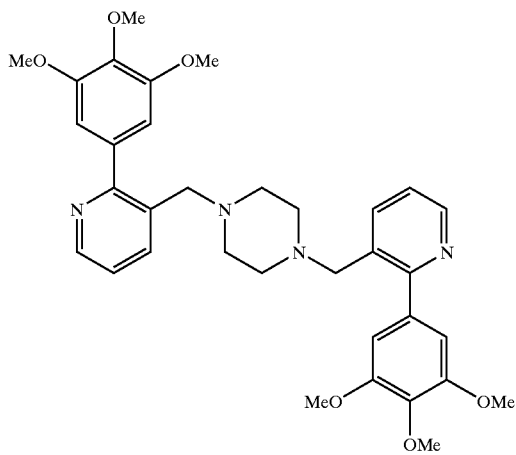

3-Chloromethyl-2-(3,4,5-trimethoxyphenyl) pyridine (241 mg) and piperazine (35 mg) were reacted in the same manner as in Example 1 to obtain the title compound as a free base.

Yield: 96 mg (40%). $^1$H-NMR (400 MHz, CDCl$_3$) δ: 2.45 (br, 8H), 3.89 (s, 12H), 3.90 (s, 6H), 6.92 (s, 4H), 7.25(dd, 2H, J=7.8 Hz, 4.9 Hz), 7.27 (s, 4H), 7.79(dd, 2H, J=7.8 Hz, 1.7 Hz), 8.58 (dd, 2H, J=4.9 Hz, 1.7 Hz). m/z (EI): 600 [M$^+$].

EXAMPLE 8

Synthesis of N,N'-bis[ [2-(3,4,5-Trimethoxyphenyl)pyridin-3-yl]methyl]homopiperazine

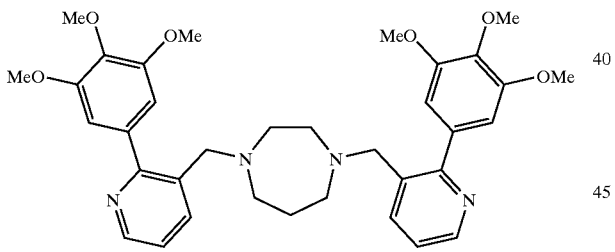

3-Chloromethyl-2-(3,4,5-trimethoxyphenyl)pyridine (311 mg) and homopiperazine (53 mg) were reacted in the same manner as in Example 1 to obtain the title compound as a free base.

Yield: 159 mg (52%). $^1$H-NMR (400 MHz, CDCl$_3$) δ: 1.68–1.73 (m, 2H), 2.57 (s, 4H), 2.63 (t, 4H, J=6.0 Hz), 3.89 (s, 12H), 3.90 (s, 6H), 6.77 (s, 4H), 7.26(dd, 2H, J=7.7 Hz, 4.6 Hz), 7.27 (s, 4H), 7.90(dd, 2H, J=7.7 Hz, 1.7 Hz), 8.55(dd, 2H, J=4.6 Hz, 1.7 Hz). m/z (EI): 614 [M$^+$].

PREPARATION EXAMPLE 13

Synthesis of ethyl 2-(3,4,5-Trimethoxyphenyl)-isonicotinate 3,4,5-Trimethoxyphenylboronic acid (15.29 g) and ethyl 2-chloroisonicotinate (13.39 g) were reacted in the same manner as in Preparation Example 1 to obtain the title compound.

Yield: 19.36 g (85%). $^1$H-NMR (400 MHz, CDCl$_3$) δ: 1.45 (t, 3H, J=7.0 Hz), 3.92 (s, 3H), 3.99 (s, 6H), 4.46 (q, 2H, J=7.0 Hz), 7.30 (s, 2H), 7.76(dd, 1H, J=5.1 Hz, 1.6 Hz), 8.24(dd, 1H, J=1.6 Hz, 0.8 Hz), 8.81(dd, 1H, J=5.1 Hz, 0.8 Hz).

PREPARATION EXAMPLE 14

Synthesis of 4-Hydroxymethyl-2-(3,4,5-trimethoxyphenyl)-pyridine

Ethyl 2-(3,4,5-trimethoxyphenyl)isonicotinate (17.21 g) was treated in the same manner as in Preparation Example 2 to obtain the title compound.

Yield: 11.78 g (79%). $^1$H-NMR (400 MHz, CDCl$_3$) δ: 3.90 (s, 3H), 3.95 (s, 6H), 4.79 (s, 2H), 7.19 (d, 1H, J=5.1 Hz), 7.21 (s, 2H),J 7.66 (s, 1H), 8.60 (d, 1H, J=5.1 Hz).

PREPARATION EXAMPLE 15

Synthesis of 4-Chloromethyl-2-(3,4,5-trimethoxyphenyl)-pyridine

4-Hydroxymethyl-2-(3,4,5-trimethoxyphenyl)pyridine (8.26 g) was treated in the same manner as in Preparation Example 3 to obtain the title compound.

Yield: 7.78 g (88%). $^1$H-NMR (400 MHz, CDCl$_3$) δ: 3.91 (s, 3H), 3.97 (s, 6H), 4.61 (s, 2H), 7.24 (s, 2H), 7.26 (d, 1H, J=5.1 Hz), 7.68 (s, 1H), 8.67 (d, 1H, J=5.1 Hz).

EXAMPLE 9

Synthesis of N,N'-bis[[2-(3,4,5-Trimethoxyphenyl)pyridin-4-yl]methyl]piperazine

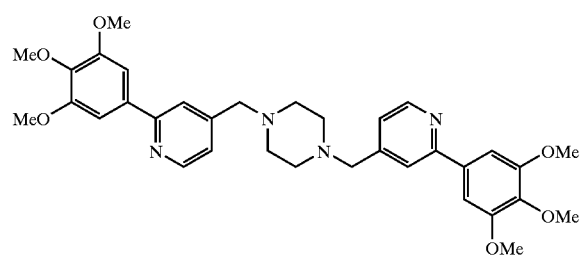

4-Chloromethyl-2-(3,4,5-trimethoxyphenyl)pyridine (100 mg) and piperazine (15 mg) were reacted in the same manner as in Example 1 to obtain the title compound as a free base.

Yield: 93 mg (91%). $^1$H-NMR (400 MHz, CDCl$_3$) δ: 2.55 (br, 8H), 3.59 (s, 4H), 3.90 (s, 6H), 3.97 (s, 12H), 7.22 (d, 2H, J=5.1 Hz), 7.24 (s, 4H), 7.64 (s, 2H), 8.59 (d, 2H, J=5.1 Hz). m/z (EI): 600 [M$^+$].

EXAMPLE 10

Synthesis of N,N'-bis[[2-(3,4,5-Trimethoxyphenyl)pyridin-4-yl]methyl]homopiperazine

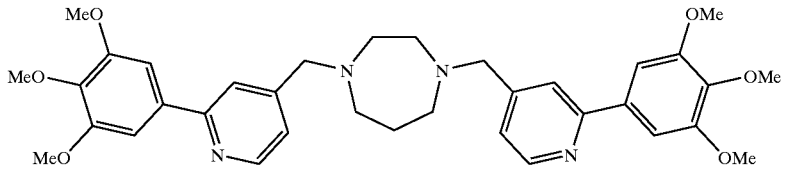

4-Chloromethyl-2-(3,4,5-trimethoxyphenyl)pyridine (100 mg) and homopiperazine (17 mg) were reacted in the same manner as in Example 1 to obtain the title compound as a free base.

Yield: 101 mg (97%). $^1$H-NMR (400 MHz, CDCl$_3$) δ: 1.85–1.88 (m, 2H), 2.73–2.90 (m, 8H), 3.72 (s, 4H), 3.89 (s, 6H), 3.96 (s, 12H), 7.24 (br, 6H), 7.66 (s, 2H), 8.58 (d, 2H, J=4.9 Hz). m/z (EI): 614 [M$^+$].

PREPARATION EXAMPLE 16

Synthesis of Ethyl 5-(3,4,5-Trimethoxyphenyl)nicotinate 3,4,5-Trimethoxyphenylboronic acid (6.36 g) and ethyl 5-bromonicotinate (6.90 g) were reacted in the same manner as in Preparation Example 1 to obtain the title compound.

Yield: 7.19 g (76%). $^1$H-NMR (400 MHz, CDCl$_3$) δ: 1.44 (t, 3H, J=7.1 Hz), 3.91 (s, 3H), 3.95 (s, 6H), 4.46 (q, 2H, J=7.1 Hz), 6.79 (s, 2H), 8.44 (t, 1H, J=2.1 Hz), 8.96 (d, 1H, J=2.1 Hz), 9.18 (d, 1H, J=1.8 Hz).

PREPARATION EXAMPLE 17

Synthesis of 3-Hydroxymethyl-5-(3,4,5-trimethoxyphenyl)-pyridine

Ethyl 5-(3,4,5-trimethoxyphenyl)nicotinate (7.19 g) was treated in the same manner as in Preparation Example 2 to obtain the title compound.

Yield: 3.83 g (61.3%). $^1$H-NMR (400 MHz, CDCl$_3$) δ: 3.88 (s, 3H), 3.89 (s, 6H), 4.39 (br, 1H), 4.80 (s, 2H), 6.72 (s, 2H), 7.89 (t, 1H, J=1.2 Hz), 8.47 (d, 1H, J=2.1 Hz), 8.63 (d, 1H, J=2.2 Hz).

PREPARATION EXAMPLE 18

Synthesis of 3-Chloromethyl-5-(3,4,5-trimethoxyphenyl)-pyridine

3-Hydroxymethyl-5-(3,4,5-trimethoxyphenyl)pyridine (2.85 g) was treated in the same manner as in Preparation Example 3 to obtain the title compound.

Yield: 1.97 g (65%). $^1$H-NMR (400 MHz, CDCl$_3$) δ: 3.90 (s, 3H), 3.94 (s, 6H), 4.67 (s, 2H), 6.75 (s, 2H), 7.87 (t, 1H, J=2.1 Hz), 8.59 (d, 1H, J=2.0 Hz), 8.76 (d, 1H, J=2.1 Hz).

EXAMPLE 11

Synthesis of N,N'-bis[[5-(3,4,5-Trimethoxyphenyl)pyridin-3-yl]methyl]piperazine

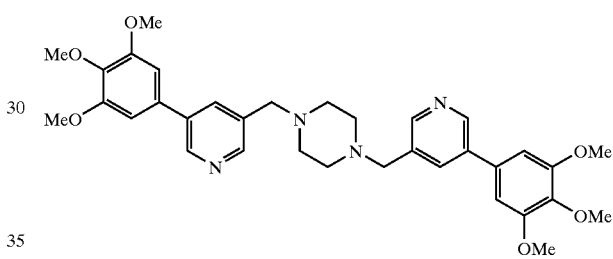

3-Chloromethyl-5-(3,4,5-trimethoxyphenyl)pyridine (70 mg) and piperazine (10 mg) were reacted in the same manner as in Example 1 to obtain the title compound as a free base.

Yield: 47 mg (65%). $^1$H-NMR (400 MHz, CDCl$_3$) δ: 2.53 (br, 8H), 3.59 (s, 4H), 3.90 (s, 6H), 3.94 (s, 12H), 6.76 (s, 4H), 7.79 (s, 2H), 8.51 (s, 2H), 8.70 (s, 2H). m/z (EI): 600 [M$^+$].

EXAMPLE 12

Synthesis of N,N'-bis[[5-(3,4,5-Trimethoxyphenyl)pyridin-3-yl]methyl]homopiperazine

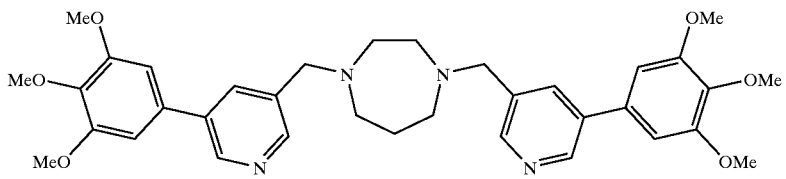

3-Chloromethyl-5-(3,4,5-trimethoxyphenyl)pyridine (70 mg) and homopiperazine (12 mg) were reacted in the same manner as in Example 1 to obtain the title compound as a free base. Yield: 56 mg (76%). $^1$H-NMR (400 MHz, CDCl$_3$) δ: 1.85 (br, 2H), 2.73 (br, 4H), 2.79 (t, 4H, J=5.9 Hz), 3.73 (s, 4H), 3.90 (s, 6H), 3.94 (s, 12H), 6.76 (s, 4H), 7.82 (s, 2H), 8.53 (d, 2H, J=2.0 Hz), 8.68 (d, 2H, J=2.1 Hz). m/z (EI): 614 [M$^+$].

PREPARATION EXAMPLE 19

Synthesis of Ethyl 6-(3,4,5-trimethoxyphenyl)picolinate 3,4,5-Trimethoxyphenylboronic acid (837 mg) and ethyl 6-chloropicolinate (733 mg) were reacted in the same manner as in Preparation Example 1 to obtain the title compound.

Yield: 929 mg (74%). $^1$H-NMR (400 MHz, CDCl$_3$) δ: 1.46 (t, 3H, J=7.1 Hz), 3.90 (s, 3H), 3.98 (s, 6H), 4.49 (q, 2H, J=7.1 Hz), 7.30 (s, 2H), 7.84–7.94 (m, 2H), 8.03(dd, 1H, J=7.2 Hz, 1.5 Hz).

PREPARATION EXAMPLE 20

Synthesis of 2-Hydroxymethyl-6-(3,4,5-trimethoxyphenyl)-pyridine

Ethyl 6-(3,4,5-trimethoxyphenyl)picolinate (929 mg) was treated in the same manner as in Preparation Example 2 to obtain the title compound.

Yield: 698 mg (87%). $^1$H-NMR (400 MHz, CDCl$_3$) δ: 3.91 (s, 3H), 3.97 (s, 6H), 4.82 (s, 2H), 7.17 (d, 1H, J=7.6 Hz), 7.24 (s, 2H), 7.60 (d, 1H, J=7.8 Hz), 7.75 (t, 1H, J=7.8 Hz).

PREPARATION EXAMPLE 21

Synthesis of 2-Chloromethyl-6-(3,4,5-trimethoxyphenyl)-pyridine

2-Hydroxymethyl-6-(3,4,5-Trimethoxyphenyl)pyridine (698 mg) was treated in the same manner as in Preparation Example 3 to obtain the title compound.

Yield: 727 mg (99%).

EXAMPLE 13

Synthesis of N,N'-bis[[6-(3,4,5-Trimethoxyphenyl)pyridin-2-yl]methyl]piperazine Dimaleate

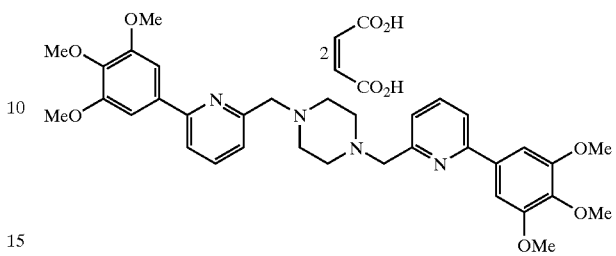

2-Chloromethyl-6-(3,4,5-trimethoxyphenyl)pyridine (353 mg) and piperazine (52 mg) were reacted in the same manner as in Example 1 to obtain a free base of the title compound. This compound was dissolved in methanol, and to the solution maleic acid was added to covert it into the title compound.

Yield: 403 mg (81%). $^1$H-NMR (400 MHz, DMSO-d$_6$, 120° C.) δ: 3.14 (s, 8H), 3.79 (s, 6H), 3.89 (s, 12H), 4.13 (s, 4H), 6.11 (s, 4H), 7.36–7.38 (m, 2H), 7.37 (s, 4H), 7.80–7.86 (m, 4H). m/z (EI): 600 [M$^+$].

EXAMPLE 14

Synthesis of N,N'-bis[[6-(3,4,5-Trimethoxyphenyl)pyridin-2-yl]methyl]homopiperazine Difumarate

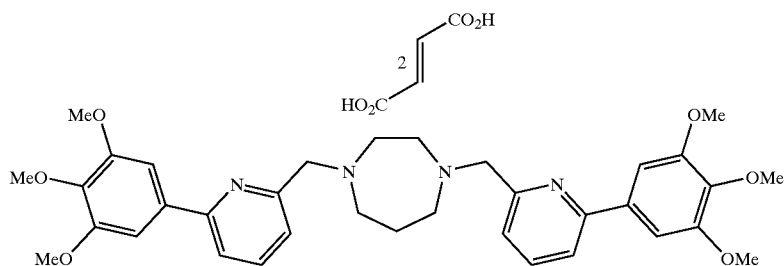

2-Chloromethyl-6-(3,4,5-trimethoxyphenyl)pyridine (374 mg) and homopiperazine (64 mg) were reacted in the same manner as in Example 1 to obtain a free base of the title compound. This compound was dissolved in methanol, and to the solution fumaric acid was added to covert it into the title compound.

Yield: 293 mg (58%). $^1$H-NMR (400 MHz, DMSO-d$_6$, 120° C.) δ: 1.86(quint, 2H, J=5.9 Hz), 2.94 (s, 4H), 2.94 (t, 4H, J=5.9 Hz), 3.77 (s, 6H), 3.87 (s, 12H), 3.94 (s, 4H), 6.63 (s, 4H), 7.35 (s, 4H), 7.36 (d, 2H, J=5.4 Hz), 7.71 (d, 2H, J=6.8 Hz), 7.76 (t, 2H, J=7.6 Hz). m/z (EI): 614 [M$^+$].

PREPARATION EXAMPLE 22

Synthesis of 4-bromopyridine-N-oxide

After 4-Bromopyridine hydrochloride (2.88 g) and potassium carbonate (2.46 g) were added to dichloromethane (50 mL), and the mixture was stirred for 2 hours, 3-chloroperbenzoic acid (5.11 g) was further added to the mixture to conduct stirring at room temperature for 1 hour. Ethyl acetate was added to the reaction mixture, and the resultant mixture was stirred to separate insoluble matter by filtration. The filtrate was concentrated under reduced pressure, and the residue was purified by column chromatography on silica gel (ethyl acetate:hexane=50:1 to chloroform:methanol=20:1) to obtain the title compound.

Yield: 2.25 g (87%).

PREPARATION EXAMPLE 23

Synthesis of 4-(3,4,5-Trimethoxyphenyl)pyridine-N-oxide 3,4,5-Trimethoxyphenylboronic acid (2.49 g) and 4-bromopyridine-N-oxide (2.25 g) were reacted in the same manner as in Preparation Example 1 to obtain the title compound.

Yield: 2.69 g (88%). $^1$H-NMR (400 MHz, CDCl$_3$) δ: 3.90 (s, 3H), 3.93 (s, 6H), 6.76 (s, 2H), 7.47 (d, 2H, J=7.1 Hz), 8.25 (d, 2H, J=7.1 Hz).

PREPARATION EXAMPLE 24

Synthesis of 2-Chloro-4-(3,4,5-trimethoxyphenyl)pyridine

Phosphorus oxychloride (2 mL) was added to 4-(3,4,5-Trimethoxyphenyl)pyridine-N-oxide (27 mg) at 0° C., and the mixture was stirred at 100° C. for 5 hours. The reaction mixture was concentrated under reduced pressure, and the residue was diluted with ethyl acetate and neutralized with a saturated aqueous solution of sodium hydrogencarbonate at 0° C. The neutralized product was extracted with ethyl acetate, and the extract was washed with saturated brine and dried over anhydrous sodium sulfate. The residue was purified by column chromatography on silica gel (ethyl acetate) to obtain the title compound.

Yield: 22 mg (77%). $^1$H-NMR (400 MHz, CDCl$_3$) δ: 3.91 (s, 3H), 3.94 (s, 6H), 6.79 (s, 2H), 7.39 (d, 1H, J=4.9 Hz), 7.49 (s, 1H), 8.41 (d, 1H, J=5.3 Hz).

PREPARATION EXAMPLE 25

Synthesis of 2-Methyl-4-(3,4,5-trimethoxyphenyl)pyridine

Nickel chloride (3.0 mg) was added to THF (1 mL) under an argon atmosphere, and the mixture was kept at 0° C. To the mixture, a THF solution (0.38 mL) of 0.93 M bromomethylmagnesium was slowly added, and a THF solution (2 mL) of 2-chloro-4-(3,4,5-Trimethoxyphenyl)pyridine (50 mg) was then slowly added. The mixture was stirred at 0° C. for 10 minutes and then at 70° C. for 1.5 hours. A small amount was diluted hydrochloric acid was added to the reaction mixture at 0° C. to conduct extraction with ethyl acetate. The resultant organic layer was washed with a saturated aqueous solution of sodium hydrogencarbonate and saturated brine, dried over anhydrous sodium sulfate and concentrated under reduced pressure. The residue was purified by column chromatography on silica gel (dichloromethane:methanol=15:1) to obtain the title compound.

Yield: 35 mg (75%). $^1$H-NMR (400 MHz, CDCl$_3$) δ: 2.62 (s, 3H), 3.90 (s, 3H), 3.94 (s, 6H), 6.81 (s, 2H), 7.27 (d, 1H, J=5.1 Hz), 7.32 (s, 1H), 8.52 (d, 1H, J=5.3 Hz).

PREPARATION EXAMPLE 26

Synthesis of 4-(3,4,5-Trimethoxyphenyl)pyridine-2-carboxylic Acid

2-Methyl-4-(3,4,5-trimethoxyphenyl)pyridine (830 mg) was dissolved in pyridine (4 mL), to the solution selenium dioxide (852 mg) was added, and the mixture was stirred at 120° C. for 3 days. The reaction mixture was filtered, and the filtrate was concentrated under reduced pressure. The residue was then dissolved in methanol-chloroform, and to the solution hexane was added to precipitate a product, thereby obtaining the title compound.

Yield: 587 mg (64%).

PREPARATION EXAMPLE 27

Synthesis of Methyl 4-(3,4,5-Trimethoxyphenyl)pyridine-2-carboxylate 4-(3,4,5-Trimethoxyphenyl)pyridine-2-carboxylic acid (587 mg) was dissolved in methanol (2 mL) and dichloromethane (8 mL), and to the solution 1-ethyl-3-(3-dimethylaminopropyl)carbodiimide hydrochloride (583 mg) was added, and the mixture was stirred at room temperature for 3 hours. The reaction mixture was concentrated under reduced pressure, and the residue was diluted with ethyl acetate. After the organic layer was washed with saturated brine, dried over anhydrous sodium sulfate and concentrated under reduced pressure, the residue was purified by column chromatography on silica gel (chloroform:methanol=40:1) to obtain the title compound.

Yield: 543 mg (88%).

PREPARATION EXAMPLE 28

Synthesis of 2-Hydroxymethyl-4-(3,4,5-trimethoxyphenyl)-pyridine

Methyl 4-(3,4,5-trimethoxyphenyl)pyridine-2-carboxylate (543 mg) was treated in the same manner as in Preparation Example 2 to obtain the title compound.

Yield: 429 mg (87%). $^1$H-NMR (400 MHz, CDCl$_3$) δ: 1.32 (br, 1H), 3.90 (s, 3H), 3.94 (s, 6H), 4.83 (s, 2H), 6.82 (s, 2H), 7.38 (d, 1H, J=4.9 Hz), 7.42 (s, 1H), 8.58 (d, 1H, J=5.1 Hz).

PREPARATION EXAMPLE 29

Synthesis of 2-Chloromethyl-4-(3,4,5-trimethoxyphenyl)-pyridine

2-Hydroxymethyl-4-(3,4,5-trimethoxyphenyl)pyridine (429 mg) was treated in the same manner as in Preparation Example 3 to obtain the title compound.

Yield: 374 mg (82%).

EXAMPLE 15

Synthesis of N,N'-bis[[4-(3,4,5-Trimethoxyphenyl)pyridin-2-yl]methyl]piperazine

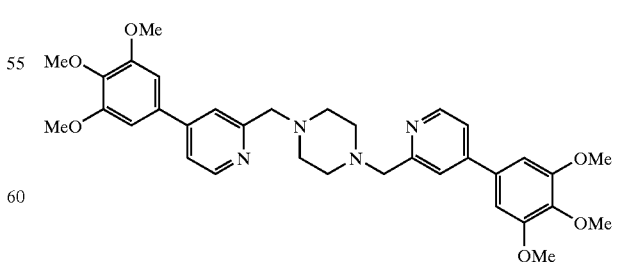

2-Chloromethyl-4-(3,4,5-trimethoxyphenyl)pyridine (195 mg) and piperazine (28 mg) were reacted in the same manner as in Example 1 to obtain the title compound.

Yield: 150 mg (79%). $^1$H-NMR (400 MHz, CDCl$_3$) δ: 2.63 (br, 8H), 3.74 (s, 4H), 3.90 (s, 6H), 3.94 (s, 12H), 6.82 (s, 4H), 7.34(dd, 2H, J=5.1 Hz, 1.7 Hz), 7.56 (s, 2H), 8.58 (d, 2H, J=5.4 Hz). m/z (EI): 600 [M$^+$].

EXAMPLE 16

Synthesis of N,N'-bis[[4-(3,4,5-Trimethoxyphenyl)pyridin-2-yl]methyl]homopiperazine

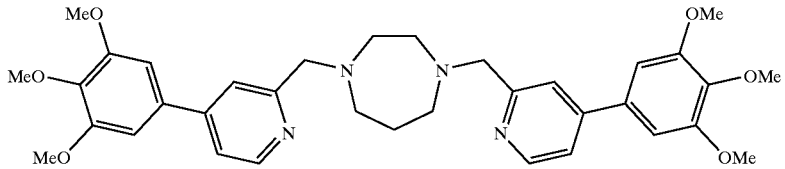

2-Chloromethyl-4-(3,4,5-trimethoxyphenyl)pyridine (195 mg) and homopiperazine (32 mg) were reacted in the same manner as in Example 1 to obtain the title compound.

Yield: 177 mg (91%). $^1$H-NMR (400 MHz, CDCl$_3$) δ: 1.88–1.91 (m, 2H), 2.84–2.89 (m, 8H), 3.88 (s, 4H), 3.90 (s, 6H), 3.94 (s, 12H), 6.83 (s, 4H), 7.33(dd, 2H, J=5.1 Hz, 1.7 Hz), 7.66 (d, 2H, J=1.2 Hz), 8.55 (d, 2H, J=4.6 Hz). m/z (EI): 614 [M$^+$].

PREPARATION EXAMPLE 30

Synthesis of Ethyl 6-(3,4,5-Trimethoxyphenyl)nicotinate 3,4,5-Trimethoxyphenylboronic acid (1.16 g) and ethyl 6-chloronicotinate (1.02 g) were reacted in the same manner as in Preparation Example 1 to obtain the title compound.

Yield: 1.42 g (82%). $^1$H-NMR (400 MHz, CDCl$_3$) δ: 1.43 (t, 3H, J=7.2 Hz), 3.92 (s, 3H), 3.98 (s, 6H), 4.44 (q, 2H, J=7.2 Hz), 7.32 (s, 2H), 7.76 (d, 1H, J=8.3 Hz), 8.33(dd, 1H, J=8.2 Hz, 2.2 Hz), 9.26 (d, 1H, J=2.2 Hz).

PREPARATION EXAMPLE 31

Synthesis of 5-Hydroxymethyl-2-(3,4,5-trimethoxyphenyl)-pyridine

Ethyl 6-(3,4,5-trimethoxyphenyl)nicotinate (658 mg) was treated in the same manner as in Preparation Example 2 to obtain the title compound.

Yield: 482 mg (85%). $^1$H-NMR (400 MHz, CDCl$_3$) δ: 3.91 (s, 3H), 3.97 (s, 6H), 4.76 (s, 2H), 7.23 (s, 2H), 7.68 (d, 1H, J=7.4 Hz), 7.78(dd, 1H, J=7.4 Hz, 2.3 Hz), 8.63 (d, 1H, J=2.3 Hz).

PREPARATION EXAMPLE 32

Synthesis of 5-Chloromethyl-2-(3,4,5-trimethoxyphenyl)-pyridine

5-Hydroxymethyl-2-(3,4,5-trimethoxyphenyl)pyridine (685 mg) was treated in the same manner as in Preparation Example 3 to obtain the title compound.

Yield: 717 mg (theoretical amount).

EXAMPLE 17

Synthesis of N,N'-bis[[2-(3,4,5-Trimethoxyphenyl)pyridin-5-yl]methyl]piperazine

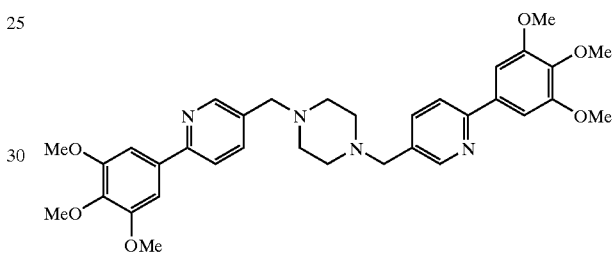

5-Chloromethyl-2-(3,4,5-Trimethoxyphenyl)pyridine (294 mg) and piperazine (43 mg) were reacted in the same manner as in Example 1 to obtain the title compound as a free base.

Yield: 198 mg (66%). $^1$H-NMR (400 MHz, CDCl$_3$) δ: 2.53 (br, 8H), 3.57 (s, 4H), 3.90 (s, 6H), 3.96 (s, 12H), 7.36 (s, 4H), 7.65 (d, 2H, J=8.1 Hz), 7.72(dd, 2H, J=8.1 Hz, 2.1 Hz), 8.58 (d, 2H, J=2.1 Hz). m/z (EI): 600 [M$^+$].

EXAMPLE 18

Synthesis of N,N'-bis[[2-(3,4,5-Trimethoxyphenyl)pyridin-5-yl]methyl]homopiperazine

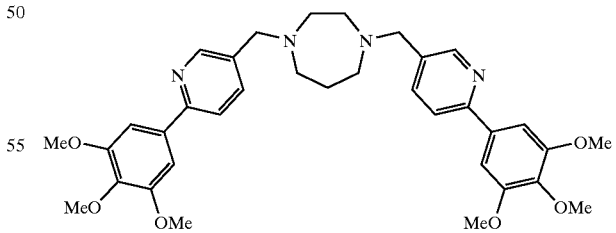

5-Chloromethyl-2-(3,4,5-trimethoxyphenyl)pyridine (294 mg) and homopiperazine (50 mg) were reacted in the same manner as in Example 1 to obtain the title compound as a free base.

Yield: 153 mg (49%). $^1$H-NMR (400 MHz, CDCl$_3$) δ: 1.83(quint, 2H, J=5.7 Hz), 2.71 (s, 4H), 2.77 (t, 4H, J=5.7 Hz), 3.70 (s, 4H), 3.93 (s, 6H), 3.96 (s, 12H), 7.24 (s, 4H), 7.56 (d, 2H, J=8.1 Hz), 7.74(dd, 2H, J=8.1 Hz, 2.1 Hz), 8.60 (d, 2H, J=2.1 Hz). m/z (EI): 614 [M⁺].

PREPARATION EXAMPLE 33

Synthesis of 2-(3,4,5-Trimethoxyphenyl)pyridine-4-carboaldehyde

4-Hydroxymethyl-2-(3,4,5-Trimethoxyphenyl)pyridine (1.01 g) was dissolved in benzene (10 mL), and to the solution activated manganese dioxide (purity: 85%, 3.78 g) was added. The mixture was stirred at room temperature for 5 hours, and activated manganese dioxide (purity: 85%, 3.78 g) was additionally added. The mixture was stirred overnight. The reaction mixture was filtered, and the filtrate was concentrated under reduced pressure. The residue was purified by column chromatography on silica gel (hexane:ethyl acetate=1:1) to obtain the title compound.

Yield: 507 mg (50%). $^1$H-NMR (400 MHz, CDCl$_3$) δ: 3.92 (s, 3H), 3.99 (s, 6H), 7.32 (s, 2H), 7.62(dd, 1H, J=4.9 Hz, 1.1 Hz), 8.09 (t, 1H, J=1.1 Hz), 8.93(dd, 1H, J=4.9 Hz, 1.1 Hz), 10.16 (s, 1H).

PREPARATION EXAMPLE 34

Synthesis of Ethyl 3-[2-(3,4,5-Trimethoxyphenyl)-pyridin-4-yl]propenoate 2-(3,4,5-Trimethoxyphenyl)pyridine-4-carboaldehyde (507 mg) and ethyl diethylphosphonoacetate (570 μL) were dissolved in tert-butanol (16 mL), and to the solution potassium carbonate (438 mg) was added. The mixture was stirred for 3 hours under reflux and concentrated under reduced pressure. The residue was dissolved in chloroform, and the solution was washed with saturated brine, dried over anhydrous magnesium sulfate and then concentrated under reduced pressure. The residue was purified by column chromatography on silica gel (hexane:ethyl acetate=1:1) to obtain the title compound.

Yield: 579 mg (89%). $^1$H-NMR (400 MHz, CDCl$_3$) δ: 1.37 (t, 3H, J=7.7 Hz), 3.92 (s, 3H), 3.98 (s, 6H), 4.31 (q, 2H, J=7.7 Hz), 6.66 (d, 1H, J=16.0 Hz), 7.25 (s, 2H), 7.31(dd, 1H, J=5.1 Hz, 1.6 Hz), 7.68 (d, 1H, J=16.0 Hz), 7.72 (d, 1H, J=1.6 Hz), 8.70 (d, 1H, J=5.1 Hz).

PREPARATION EXAMPLE 35

Synthesis of Ethyl 3-[2-(3,4,5-trimethoxyphenyl) pyridin-4-yl]propionate

Ethyl 3-[2-(3,4,5-trimethoxyphenyl)pyridin-4-yl] propenoate (579 mg) was dissolved in methanol (20 mL), 10% palladium on carbon (60 mg) was added to the solution, and the mixture was stirred at room temperature for 6 hours under a hydrogen atmosphere. The catalyst was removed by filtration, and the filtrate was concentrated under reduced pressure to obtain the title compound.

Yield: 521 mg (90%). $^1$H-NMR (400 MHz, CDCl$_3$) δ: 1.25 (t, 3H, J=7.1 Hz), 2.70 (t, 2H, J=7.6 Hz), 3.02 (t, 2H, J=7.6 Hz), 3.90 (s, 3H), 3.97 (s, 6H), 4.15 (q, 2H, J=7.1 Hz), 7.08(dd, 1H, J=5.0 Hz, 1.6 Hz), 7.22 (s, 2H), 7.52 (d, 1H, J=1.6 Hz), 8.57 (d, 1H, J=5.0 Hz).

PREPARATION EXAMPLE 36

Synthesis of 4-(3-Hydroxypropyl)-2-(3,4,5-trimethoxy-phenyl)pyridine

Ethyl 3-[2-(3,4,5-trimethoxyphenyl)pyridin-4-yl] propionate (521 mg) was treated in the same manner as in Preparation Example 2 to obtain the title compound.

Yield: 486 mg (theoretical amount). $^1$H-NMR (400 MHz, CDCl$_3$) δ: 1.92–2.00 (m, 2H), 2.80 (t, 2H, J=7.7 Hz), 3.73 (t, 2H, J=6.2 Hz), 3.90 (s, 3H), 3.97 (s, 6H), 7.08(dd, 1H, J=5.1 Hz, 1.7 Hz), 7.22 (s, 2H), 7.52(dd, 1H, J=1.7 Hz, 0.7 Hz), 8.56(dd, 1H, J=5.1 Hz, 0.7 Hz).

PREPARATION EXAMPLE 37

Synthesis of 4-(3-Methanesulfonyloxypropyl)-2-(3,4,5-trimethoxyphenyl)pyridine 4-(3-Hydroxypropyl)-2-(3,4,5-Trimethoxyphenyl)-pyridine (486 mg) was dissolved in chloroform (10 mL), and to the solution methanesulfonyl chloride (186 μL) and triethylamine (400 μL) were added, and the mixture was stirred overnight at room temperature. The reaction mixture was diluted with chloroform, washed with water and saturated brine, dried over anhydrous magnesium sulfate, and then concentrated under reduced pressure. The residue was purified by column chromatography on silica gel (hexane:ethyl acetate=1:1) to obtain the title compound.

Yield: 549 mg (90%).

EXAMPLE 19

Synthesis of N,N'-bis[3-[2-(3,4,5-Trimethoxyphenyl)-pyridin-4-yl]propyl ]piperazine Difumarate

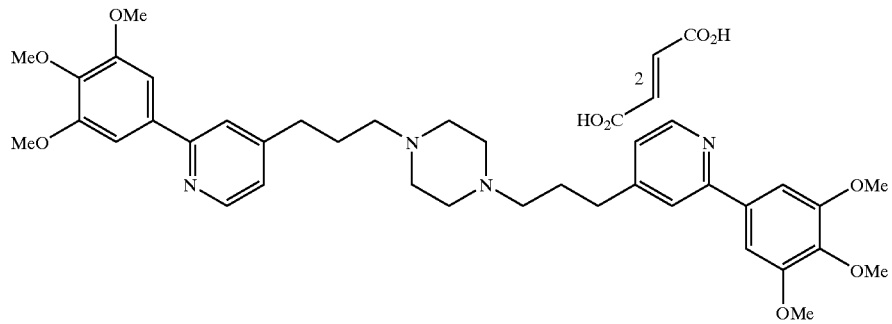

4-(3-Methanesulfonyloxypropyl)-2-(3,4,5-trimethoxyphenyl)pyridine (259 mg) and piperazine (29 mg) were reacted in the same manner in Example 1 to obtain a free base of the title compound. This compound was dissolved in methanol, and to the solution fumaric acid was added to convert it into the title compound.

Yield: 114 mg (38%). $^1$H-NMR (400 MHz, DMSO-d$_6$, 120° C.) δ: 1.79–1.87 (m, 4H), 2.39 (t, 4H, J=7.1 Hz), 2.47

(s, 8H), 2.70 (t, 4H, J=7.3 Hz), 3.77 (s, 6H), 3.88 (s, 12H), 6.63 (s, 4H), 7.11(dd, 2H, J=4.9 Hz, 1.6 Hz), 7.34 (s, 4H), 7.67(dd, 2H, J=1.6 Hz, 0.7 Hz), 8.48(dd, 2H, J=4.9 Hz, 0.7 Hz). m/z (EI): 654 [M$^+$−2].

EXAMPLE 20

Synthesis of N,N'-bis[3-[2-(3,4,5-Trimethoxyphenyl)-pyridin-4-yl]propyl]homopiperazine Difumarate

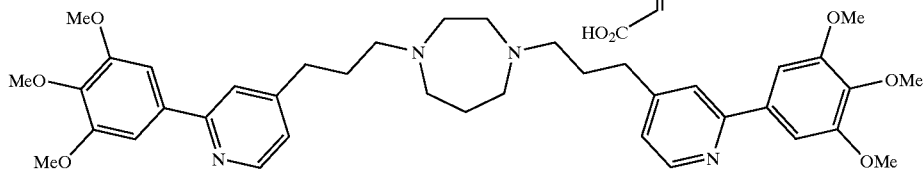

4-(3-Methanesulfonyloxypropyl)-2-(3,4,5-trimethoxyphenyl)pyridine (261 mg) and homopiperazine (34 mg) were reacted in the same manner in Example 1 to obtain a free base of the title compound. This compound was dissolved in methanol, and to the solution fumaric acid was added to convert it into the title compound.

Yield: 66 mg (22%). $^1$H-NMR (400 MHz, DMSO-d$_6$, 120° C.) δ: 1.76(quint, 2H, J=7.9 Hz), 1.79–1.87 (m, 4H), 2.57 (t, 4H, J=7.1 Hz), 2.70 (t, 4H, J=7.6 Hz), 2.73 (t, 4H, J=7.9 Hz), 2.74 (s, 4H), 3.77 (s, 6H), 3.87 (s, 12H), 6.61 (s, 4H), 7.10 (d, 2H, J=4.6 Hz), 7.34 (s, 4H), 7.66 (s, 2H), 8.47 (d, 2H, J=4.9 Hz). m/z (EI): 668 [M$^+$−2].

PREPARATION EXAMPLE 38

Synthesis of 2-(3,4,5-Trimethoxyphenyl)pyridine-3-carboaldehyde

3-Hydroxymethyl-2-(3,4,5-trimethoxyphenyl)pyridine (958 mg) was treated in the same manner as in Preparation Example 33 to obtain the title compound.

Yield: 561 mg (59%).

PREPARATION EXAMPLE 39

Synthesis of Ethyl 3-[2-(3,4,5-trimethoxyphenyl)pyridin-3-yl]propenoate 2-(3,4,5-Trimethoxyphenyl)pyridine-3-carboaldehyde (517 mg) was treated in the same manner as in Preparation Example 34 to obtain the title compound.

Yield: 740 mg (theoretical amount).

PREPARATION EXAMPLE 40

Synthesis of Ethyl 3-[2-(3,4,5-trimethoxyphenyl)pyridin-3-yl]propionate

Ethyl 3-[2-(3,4,5-trimethoxyphenyl)pyridin-3-yl]propenoate (740 mg) was treated in the same manner as in Preparation Example 35 to obtain the title compound.

Yield: 167 mg (26%). $^1$H-NMR (400 MHz, CDCl$_3$) δ: 1.20 (t, 3H, J=7.1 Hz), 2.50 (t, 2H, J=7.6 Hz), 3.03 (t, 2H, J=8.0 Hz), 3.90 (s, 9H), 4.09 (q, 2H, J=7.1 Hz), 6.69 (s, 2H), 7.23(dd, 1H, J=7.8 Hz, 4.9 Hz), 7.63(dd, 1H, J=7.8 Hz, 1.6 Hz), 8.53(dd, 1H, J=4.8 Hz, 1.6 Hz).

PREPARATION EXAMPLE 41

Synthesis of 3-(3-Hydroxypropyl)-2-(3,4,5-Trimethoxy-phenyl)pyridine

Ethyl 3-[2-(3,4,5-trimethoxyphenyl)pyridin-3-yl]propionate (167 mg) was treated in the same manner as in Preparation Example 2 to obtain the title compound.

Yield: 135 mg (91%). $^1$H-NMR (400 MHz, CDCl$_3$) δ: 1.75–1.83 (m, 2H), 2.78 (t, 2H, J=7.9 Hz), 3.59 (t, 2H, J=6.3 Hz), 3.88 (s, 6H), 3.89 (s, 3H), 6.69 (s, 2H), 7.22–7.24 (m, 1H), 7.64 (d, 1H, J=7.6 Hz), 8.51 (d, 1H, J=3.3 Hz).

PREPARATION EXAMPLE 42

Synthesis of 3-(3-Methanesulfonyloxypropyl)-2-(3,4,5-Trimethoxyphenyl)pyridine 3-(3-Hydroxypropyl)-2-(3,4,5-trimethoxyphenyl)-pyridine (64 mg) was treated in the same manner as in Preparation Example 37 to obtain the title compound.

Yield: 80 mg (theoretical amount).

EXAMPLE 21

Synthesis of N,N'-bis[3-[2-(3,4,5-Trimethoxyphenyl)-pyridin-3-yl]propyl]piperazine

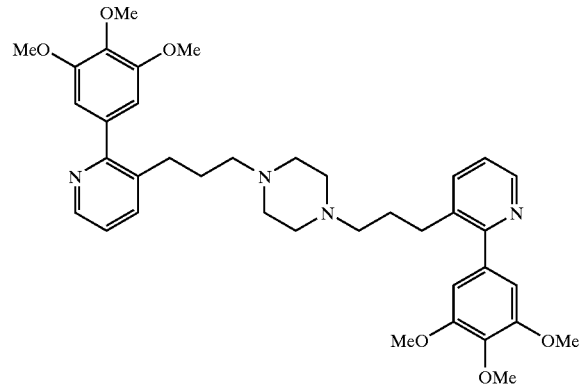

3-(3-Methanesulfonyloxypropyl)-2-(3,4,5-Trimethoxyphenyl)pyridine (80 mg) and piperazine (9 mg) were reacted in the same manner in Example 1 to obtain the title compound as a free base.

Yield: 14 mg (19%). $^1$H-NMR (400 MHz, CDCl$_3$) δ: 1.65–1.72 (m, 4H), 2.24–2.32 (m, 12H), 2.68 (t, 4H, J=8.0 Hz), 3.88 (s, 18H), 6.66 (s, 4H), 7.22(dd, 2H, J=7.7 Hz, 4.6 Hz), 7.62(dd, 2H, J=7.6 Hz, 1.5 Hz), 8.50(dd, 2H, J=4.8 Hz, 1.7 Hz). m/z (EI): 654 [M$^+$−2].

PREPARATION EXAMPLE 43

Synthesis of Ethyl 2-(3,4,5-Trimethoxyphenylethynyl)-pyridine-4-carboxylate 3,4,5-Trimethoxyphenylacetylene (1.80 g), ethyl 2-chloroisonicotinate (2.08 g) and copper iodide (71 mg) were dissolved in a mixed solvent of DMF (4 mL) and triethylamine (8 mL), and to the solution bis-(triphenylphosphine)palladium dichloride (0) (131 mg) was added, and the mixture was stirred at 45° C. for 4 hours under an argon atmosphere. The reaction mixture was diluted with ethyl acetate, washed with 2 M hydrochloric acid, water and saturated brine, dried over anhydrous sodium sulfate. After concentrating the reaction mixture under reduced pressure, the residue was purified by column chromatography on silica gel (hexane:ethyl acetate=4:1 to 3:1) to obtain the title compound.

Yield: 1.50 g (47%). $^1$H-NMR (400 MHz, CDCl$_3$) δ: 1.43 (t, 3H, J=7.1 Hz), 3.88 (s, 6H), 3.89 (s, 3H), 4.44 (q, 2H, J=7.1 Hz), 6.87 (s, 2H), 7.79(dd, 1H, J=5.1 Hz, 1.6 Hz), 8.07 (s, 1H), 8.76 (d, 1H, J=5.1 Hz).

PREPARATION EXAMPLE 44

Synthesis of 2-(3,4,5-Trimethoxyphenylethynyl)pyridine-4-carboxylic Acid

Ethyl 2-(3,4,5-trimethoxyphenylethynyl)pyridine-4-carboxylate (1.40 g) was suspended in methanol (100 mL), to the suspension lithium hydroxide hydrate (189 mg) was added, and the mixture was stirred at room temperature for 4 hours. The reaction mixture was concentrated under reduced pressure, water was added to the residue and the resultant mixture was neutralized with 1 M hydrochloric acid. After the reaction mixture was cooled with ice, crystals precipitated were collected by filtration to obtain the title compound as colorless crystals.

Yield: 1.21 g (94%). $^1$H-NMR (400 MHz, CDCl$_3$) δ: 3.79 (s, 3H), 3.86 (s, 6H), 6.98 (s, 2H), 7.77(dd, 1H, J=5.1 Hz, 1.7 Hz), 7.99 (s, 1H), 8.55 (d, 1H, J=5.1 Hz).

PREPARATION EXAMPLE 45

Synthesis of 4-Hydroxymethyl-2-(3,4,5-trimethoxyphenyl-ethynyl)pyridine 2-(3,4,5-Trimethoxyphenylethynyl)pyridine-4-carboxylic acid (90 mg) was dissolved in THF (6 mL), and to the solution triethylamine (35 mg) was added at 0° C. under an argon atmosphere. Ethyl chloroformate (34 mg) was then added to the mixture, and the mixture was stirred for 1 hour. Ethyl acetate was added to the reaction mixture, and the mixture was washed with water and saturated brine and dried over anhydrous sodium sulfate. After concentrating the reaction mixture, the residue was dissolved in THF (2 mL), and to the solution an aqueous solution (1 mL) of sodium borohydride (16 mg) was added at 0° C., and the resultant mixture was stirred for 1 hour. The reaction mixture was extracted with ethyl acetate, and the resultant organic layer was washed with saturated brine and dried over anhydrous sodium sulfate. After concentrating the organic layer under reduced pressure, the residue was purified by column chromatography on silica gel (hexane:ethyl acetate=1:1 to ethyl acetate) to obtain the title compound.

Yield: 85 mg (99%). $^1$H-NMR (400 MHz, CDCl$_3$) δ: 2.06 (br, 1H), 3.87 (s, 6H), 3.89 (s, 3H), 4.76 (s, 2H), 6.85 (s, 2H), 7.24 (d, 1H, J=5.1 Hz), 7.54 (s, 1H), 8.57 (d, 1H, J=5.1 Hz).

PREPARATION EXAMPLE 46

Synthesis of 4-Chloromethyl-2-(3,4,5-trimethoxyphenyl-ethynyl)pyridine

4-Hydroxymethyl-2-(3,4,5-trimethoxyphenylethynyl)-pyridine (483 mg) was treated in the same manner as in Preparation Example 3 to obtain the title compound.

Yield: 484 mg (94%). $^1$H-NMR (400 MHz, CDCl$_3$) δ: 3.88 (s, 6H), 3.89 (s, 3H), 4.58 (s, 2H), 6.90 (s, 2H), 7.35 (d, 1H, J=5.1 Hz), 7.61 (s, 1H), 8.63 (d, 1H, J=5.1 Hz).

EXAMPLE 22

Synthesis of N,N'-bis[[2-(3,4,5-Trimethoxyphenylethynyl)-pyridin-4-yl]m ethyl] piperazine

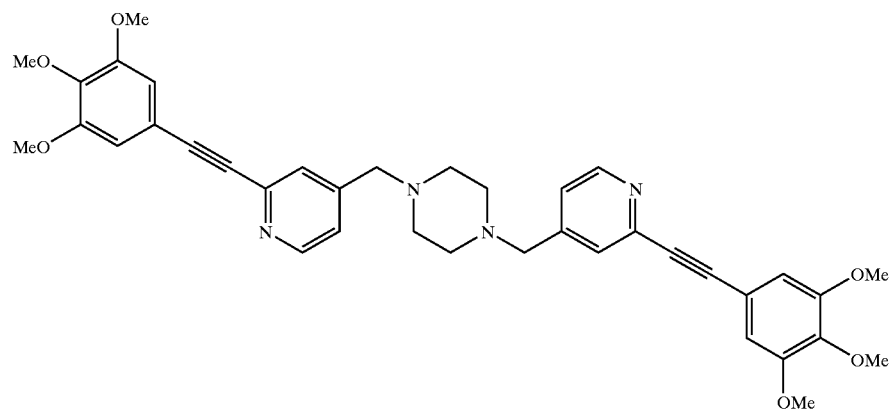

4-Chloromethyl-2-(3,4,5-Trimethoxyphenylethynyl)-pyridine (254 mg) and piperazine (31 mg) were reacted in the same manner in Example 1 to obtain the title compound as a free base.

Yield: 182 mg (78%). $^1$H-NMR (400 MHz, CDCl$_3$) δ: 2.52 (br, 8H), 3.52 (s, 4H), 3.87 (s, 12H), 3.88 (s, 6H), 6.85 (s, 4H), 7.22 (d, 2H, J=4.1 Hz), 7.52 (s, 2H), 8.40 (d, 2H, J=5.1 Hz). m/z (EI): 648 [M$^+$].

EXAMPLE 23

Synthesis of N,N'-bis[[2-(3,4,5-Trimethoxyphenylethynyl)-pyridin-4-yl]m ethyl] homopiperazine

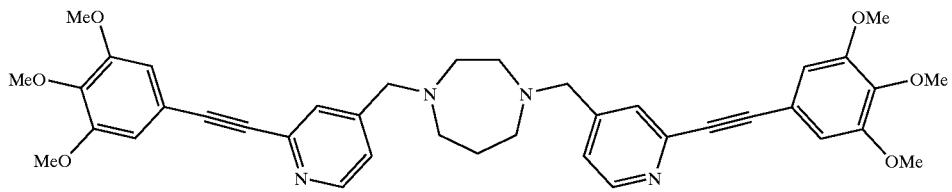

4-Chloromethyl-2-(3,4,5-Trimethoxyphenylethynyl)-pyridine (230 mg) and homopiperazine (32 mg) were reacted in the same manner in Example 1 to obtain the title compound as a free base.

Yield: 67 mg (31%). $^1$H-NMR (400 MHz, CDCl$_3$) δ: 1.83–1.86 (m, 2H), 2.70–2.78 (m, 8H), 3.67 (s, 4H), 3.87 (s, 12H), 3.88 (s, 6H), 6.85 (s, 4H), 7.25 (d, 2H, J=4.1 Hz), 7.52 (s, 2H), 8.54 (d, 2H, J=4.1 Hz). m/z (EI): 662 [M$^+$].

PREPARATION EXAMPLE 47

Synthesis of 4-Hydroxy-6-methylpyrimidine

4-Hydroxy-2-mercapto-6-methylpyrimidine (3.0 g) was dissolved in a mixed solvent of ethanol (50 mL) and aqueous ammonia (10 mL). Raney nickel (R=100, wet type, 6.0 g) was added to the solution, and the mixture was stirred at 90° C. for 2 hours. The reaction mixture was filtered through celite, and the filtrate was concentrated under reduced pressure. Water was then added to the residue to conduct extraction with ethyl acetate. The resultant organic layer was washed with saturated brine, dried over anhydrous sodium sulfate and concentrated under reduced pressure. The resultant crude crystals were recrystallized from chloroform-ether to obtain the title compound.

Yield: 1.20 g (52%). $^1$H-NMR (400 MHz, CDCl$_3$) δ: 2.30 (s, 3H), 6.29 (s, 1H), 8.07 (s, 1H).

PREPARATION EXAMPLE 48

Synthesis of 4-Chloro-6-methylpyrimidine

4-Hydroxy-6-methylpyrimidine (782 mg) was dissolved in phosphoryl chloride (6.6 mL), and the solution was heated under reflux for 1 hour. The reaction mixture was added dropwise to ice water, neutralized with an aqueous solution of 2 M sodium hydroxide and extracted with ethyl acetate. The resultant organic layer was washed with saturated brine, dried over anhydrous sodium sulfate and concentrated under reduced pressure to obtain the title compound.

Yield: 913 mg (theoretical amount).

PREPARATION EXAMPLE 49

Synthesis of 4-Methyl-6-(3,4,5-trimethoxyphenyl)-pyrimidine

4-Chloro-6-methylpyrimidine (913 mg) and 3,4,5-Trimethoxyphenylboronic acid (2.73 g) were reacted in the same manner as in Preparation Example 1 to obtain the title compound.

Yield: 920 mg (50%). $^1$H-NMR (400 MHz, CDCl$_3$) δ: 2.51 (s, 3H), 3.84 (s, 3H), 3.88 (s, 6H), 7.25 (s, 2H), 7.44 (d, 1H, J=0.6 Hz), 8.02 (d, 1H, J=1.2 Hz).

PREPARATION EXAMPLE 50

Synthesis of 6-(3,4,5-Trimethoxyphenyl)pyrimidine-4-carboaldehyde

4-Methyl-6-(3,4,5-Trimethoxyphenyl)pyrimidine (920 mg) was dissolved in dioxane (100 mL), to the solution selenium dioxide (784 mg) was added, and the mixture was stirred overnight at 105° C. Water was added to the reaction mixture to conduct extraction with ethyl acetate, and the resultant organic layer was washed with saturated brine, dried over anhydrous magnesium sulfate, and then concentrated under reduced pressure. The residue was purified by column chromatography on silica gel (hexane:ethyl acetate=1:1) to obtain the title compound.

Yield: 492 mg (51%). $^1$H-NMR (400 MHz, CDCl$_3$) δ: 3.95 (s, 3H), 3.99 (s, 6H), 7.44 (s, 2H), 8.17 (d, 1H, J=1.4 Hz), 9.43 (d, 1H, J=1.4 Hz), 10.11 (s, 1H).

PREPARATION EXAMPLE 51

Synthesis of 4-Hydroxymethyl-6-(3,4,5-trimethoxyphenyl)-pyrimidine 6-(3,4,5-Trimethoxyphenyl)pyrimidine-4-carboaldehyde (364 mg) was dissolved in methanol (50 mL), and to the solution sodium borohydride (25 mg) was added under ice cooling, and the mixture was stirred at room temperature for 2 hours. The reaction mixture was concentrated under reduced pressure, and the residue was purified by column chromatography on silica gel (chloroform:methanol=50:1) to obtain the title compound.

Yield: 339 mg (92%). $^1$H-NMR (400 MHz, CDCl$_3$) δ: 3.93 (s, 3H), 3.98 (s, 6H), 4.84 (s, 2H), 7.37 (s, 2H), 7.68 (s, 1H), 9.18 (s, 1H).

PREPARATION EXAMPLE 52

Synthesis of 4-Chloromethyl-6-(3,4,5-trimethoxyphenyl)-pyrimidine

4-Hydroxymethyl-6-(3,4,5-trimethoxyphenyl)-pyrimidine (339 mg) was dissolved in dichloromethane (20 mL), and to the solution thionyl chloride (0.15 mL) was added dropwise under ice cooling, and the mixture was stirred for 1 hour. An aqueous solution of sodium hydroxide was added to the reaction mixture to neutralize it, and extraction was conducted with methylene chloride. The resultant organic layer was washed with saturated brine, dried over anhydrous sodium sulfate and concentrated under reduced pressure. The residue was purified by column chromatography on silica gel (hexane:ethyl acetate=1:1) to obtain the title compound.

Yield: 174 mg (60%). $^1$H-NMR (400 MHz, CDCl$_3$) δ: 3.86 (s, 3H), 3.91 (s, 6H), 4.61 (s, 2H), 7.30 (s, 2H), 7.78 (s, 1H), 9.10 (d, 1H, J=1.2 Hz).

EXAMPLE 24

Synthesis of N,N'-bis[[6-(3,4,5-Trimethoxyphenyl)-pyrimidin-4-yl]methyl]piperazine

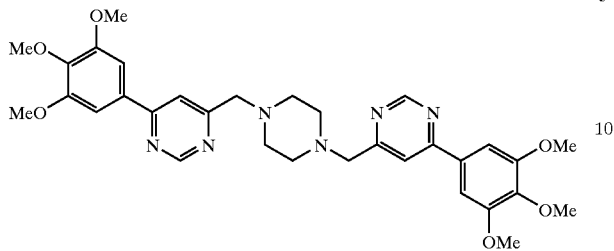

4-Chloromethyl-6-(3,4,5-trimethoxyphenyl)pyrimidine (126 mg) and piperazine (18 mg) were reacted in the same manner as in Example 1 to obtain the title compound as a free base.

Yield: 99 mg (77%). $^1$H-NMR (400 MHz, CDCl$_3$) δ: 2.68 (br, 8H), 3.73 (s, 4H), 3.93 (s, 6H), 3.98 (s, 12H), 7.37 (s, 4H), 7.79 (s, 2H), 9.16 (s, 2H) m/z (EI): 602 [M$^+$].

PREPARATION EXAMPLE 53

Synthesis of 2-Bromo–4-methylpyrimidine

2-Amino–4-methylpyrimidine (6.5 g) was dissolved in a small amount of water, and the solution concentrated hydrochloric acid (30 mL) was added dropwise under ice cooling. To the solution, sodium nitrite (4.6 g) dissolved in water was further added, and the mixture was stirred for 2 hours. Sodium bromide (30.6 g) dissolved in water was added dropwise to the reaction mixture, and the resultant mixture was warmed to room temperature and stirred for 4 hours. The reaction mixture was extracted with ethyl acetate, and the resultant organic layer was washed with saturated brine, dried over anhydrous sodium sulfate and concentrated under reduced pressure. The residue was purified by column chromatography on silica gel (hexane:ethyl acetate=9:1) to obtain the title compound.

Yield: 930 mg (9%). $^1$H-NMR (400 MHz, CDCl$_3$) δ: 2.55 (s, 3H), 7.13 (d, 1H, J=5.1 Hz), 8.48 (d, 1H, J=5.1 Hz).

PREPARATION EXAMPLE 54

Synthesis of 4-methyl-2-(3,4,5-Trimethoxyphenyl)-pyrimidine

2-Bromo–4-methylpyrimidine (1.5 g) and 3,4,5-trimethoxyphenylboronic acid (1.83 g) were reacted in the same manner as in Preparation Example 1 to obtain the title compound.

Yield: 1.49 g (67%). $^1$H-NMR (400 MHz, CDCl$_3$) δ: 2.57 (s, 3H), 3.92 (s, 3H), 3.99 (s, 6H), 7.01 (d, 1H, J=5.1 Hz), 7.77 (s, 2H), 8.61 (d, 1H, J=5.1 Hz).

PREPARATION EXAMPLE 55

Synthesis of 2-(3,4,5-Trimethoxyphenyl)pyrimidine-4-carboaldehyde

4-Methyl-2-(3,4,5-trimethoxyphenyl)-pyrimidine (1.6 g) was treated in the same manner as in Preparation Example 50 to obtain the title compound.

Yield: 1.57 g (95%). $^1$H-NMR (400 MHz, CDCl$_3$) δ: 3.87 (s, 3H), 3.92 (s, 6H), 7.56 (d, 1H, J=4.9 Hz), 7.76 (s, 2H), 8.92 (d, 1H, J=4.7 Hz), 10.03 (s, 1H)

PREPARATION EXAMPLE 56

Synthesis of 4-Hydroxymethyl-2-(3,4,5-trimethoxyphenyl)-pyrimidine 2-(3,4,5-Trimethoxyphenyl)pyrimidine-4-carboaldehyde (1.27 g) was treated in the same manner as in Preparation Example 51 to obtain the title compound.

Yield: 1.00 g (78%). $^1$H-NMR (400 MHz, CDCl$_3$) δ: 3.44 (br, 1H), 3.86 (s, 3H), 3.91 (s, 6H), 4.74 (d, 2H, J=5.1 Hz), 7.10 (d, 1H, J=5.1 Hz), 7.59 (s, 2H), 8.66 (d, 1H, J=5.1 Hz).

PREPARATION EXAMPLE 57

Synthesis of 4-Chloromethyl-2-(3,4,5-trimethoxyphenyl)-pyrimidine

4-Hydroxymethyl-2-(3,4,5-trimethoxyphenyl)-pyrimidine (1.00 g) was treated in the same manner as in Preparation Example 3 to obtain the title compound.

Yield: 1.05 g (98%). $^1$H-NMR (400 MHz, CDCl$_3$) δ: 3.93 (s, 3H), 3.99 (s, 6H), 4.68 (s, 2H), 7.40 (d, 1H, J=5.1 Hz), 7.77 (s, 2H), 8.81 (d, 1H, J=5.1 Hz).

EXAMPLE 25

Synthesis of N,N'-bis[[2-(3,4,5-Trimethoxyphenyl)-pyrimidin-4-yl]methyl]piperazine

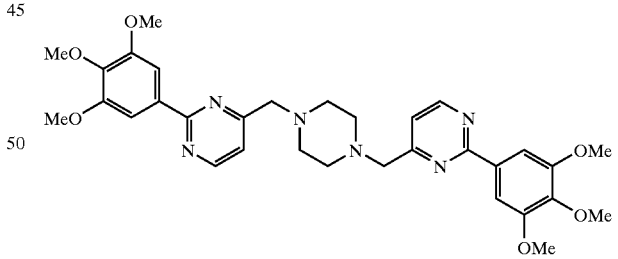

4-Chloromethyl-2-(3,4,5-trimethoxyphenyl) pyrimidine (300 mg) and piperazine (44 mg) were reacted in the same manner as in Example 1 to obtain the title compound as a free base.

Yield: 200 mg (65%). $^1$H-NMR (400 MHz, CDCl$_3$) δ: 2.60 (br, 8H), 3.68 (s, 4H), 3.84 (s, 6H), 3.91 (s, 12H), 7.30 (d, 2H, J=–5.1 Hz), 7.69 (s, 4H), 8.64 (d, 2H, J=5.1 Hz). m/z (EI): 602 [M$^+$].

EXAMPLE 26

Synthesis of N,N'-bis[[2-(3,4,5-Trimethoxyphenyl)-pyrimidin-4-yl]methyl]homopiperazine

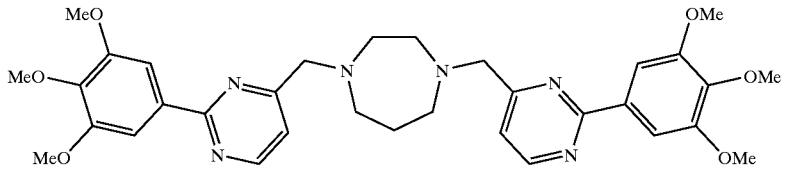

4-Chloromethyl-2-(3,4,5-trimethoxyphenyl)pyrimidine (300 mg) and homopiperazine (51 mg) were reacted in the same manner as in Example 1 to obtain the title compound as a free base.

Yield: 269 mg (87%). $^1$H-NMR (400 MHz, CDCl$_3$) δ: 1.83–1.86 (m, 2H), 2.79 (s, 4H), 2.82 (t, 4H, J=6.0 Hz), 2.83 (s, 4H), 3.84 (s, 6H), 3.91 (s, 12H), 7.35 (d, 2H, J=5.1 Hz), 7.70 (s, 4H), 8.65 (d, 2H, J=5.1 Hz). m/z (EI): 616 [M$^+$].

PREPARATION EXAMPLE 58

Synthesis of Ethyl 2-methylthio-4-(3,4,5-Trimethoxy-phenyl)pyrimidine-5-carboxylate Ethyl 4-chloro-2-methylthiopyrimidine-5-carboxylate (3.0 g) and 3,4,5-trimethoxyphenylboronic acid (2.73 g) were reacted in the same manner as in Preparation Example 1 to obtain the title compound.

Yield: 3.07 g (65%). $^1$H-NMR (400 MHz, CDCl$_3$) δ: 1.09 (t, 3H, J=7.1 Hz), 2.52 (s, 3H), 3.81 (s, 6H), 3.82 (s, 3H), 4.40 (q, 2H, J=7.2 Hz), 6.77 (s, 2H), 8.78 (s, 1H).

PREPARATION EXAMPLE 59

Synthesis of 5-Hydroxymethyl-2-methylthio-4-(3,4,5-trimethoxyphenyl)pyrimidine

Ethyl 2-methylthio-4-(3,4,5-trimethoxyphenyl)-pyrimidine-5-carboxylate (2.51 g) was treated in the same manner as in Preparation Example 2 to obtain the title compound.

Yield: 720 mg (38%). $^1$H-NMR (400 MHz, CDCl$_3$) δ: 2.62 (s, 3H), 3.91 (s, 9H), 4.68 (s, 2H), 7.09 (s, 2H), 8.61 (s, 1H).

PREPARATION EXAMPLE 60

Synthesis of 5-Hydroxymethyl-4-(3,4,5-trimethoxyphenyl)-pyrimidine

5-Hydroxymethyl-2-methylthio-4-(3,4,5-trimethoxyphenyl)pyrimidine (1.75 g) was dissolved in a mixed solvent of ethanol (50 mL) and aqueous ammonia (5 mL). Raney nickel (R=100, wet type, 17.0 g) was added to the solution, and the mixture was stirred at 90° C. for 2.5 hours. The reaction mixture was filtered through celite, and the filtrate was concentrated under reduced pressure. Water was added to the residue to conduct extraction with ethyl acetate. The resultant organic layer was washed with saturated brine, dried over anhydrous sodium sulfate and concentrated under reduced pressure. The residue was purified by column chromatography on silica gel (hexane:ethyl acetate=9:1) to obtain the title compound.

Yield: 827 mg (50%). $^1$H-NMR (400 MHz, CDCl$_3$) δ: 3.91 (s, 9H), 4.77 (s, 2H), 7.04 (s, 2H), 8.34 (s, 1H), 9.18 (s, 1H).

PREPARATION EXAMPLE 61

Synthesis of 5-Chloromethyl-4-(3,4,5-trimethoxyphenyl)-pyrimidine

5-Hydroxymethyl-4-(3,4,5-trimethoxyphenyl)-pyrimidine (827 mg) was treated in the same manner as in Preparation Example 3 to obtain the title compound.

Yield: 757 mg (86%). $^1$H-NMR (400 MHz, CDCl$_3$) δ: 3.93 (s, 3H), 3.94 (s, 6H), 4.65 (s, 2H), 7.03 (s, 2H), 8.87 (s, 1H), 9.22 (s, 1H).

EXAMPLE 27

Synthesis of N,N'-bis[[4-(3,4,5-Trimethoxyphenyl)-pyrimidin-5-yl]methyl]piperazine

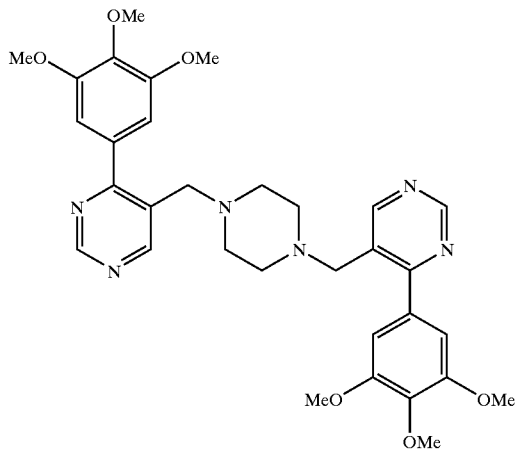

5-Chloromethyl-4-(3,4,5-trimethoxyphenyl)pyrimidine (250 mg) and piperazine (37 mg) were reacted in the same manner as in Example 1 to obtain the title compound as a free base.

Yield: 221 mg (86%). $^1$H-NMR (400 MHz, CDCl$_3$) δ: 2.53 (br, 8H), 3.52 (s, 4H), 3.92 (s, 18H), 7.17 (s, 4H), 8.72 (s, 2H), 9.12 (s, 2H). m/z (EI): 602 [M$^+$].

TEST EXAMPLE 1

Inhibitory Effect on Cell Adhesion

This test was conducted by reference to the method of Ross et al. (J. Biol. Chem., 267, 8537–8543 (1992)). More specifically, after human umbilical venous endothelial cells (HUVEC) were cultured on a 48-well plate to confluent growth, IL–1β or TNFα was added thereto. Upon elapsed time of 5 hours after the addition, U937, which is a human monocytic/histocytic cell fluorescence-labeled with PKH2

(product of Dainippon Pharmaceutical Co., Ltd.), was added in a proportion of $1 \times 10^6$ cells per well. After the plate was left at rest at room temperature for 1 hour, unadhered U937 was washed out and lysed in 1% Triton X-100 to measure a remaining fluorescence intensity (excitation wavelength: 480 nm; measuring wavelength: 530 nm). HUVEC and U937 were cultured in EGM-2 (product of Sanko Junyaku K.K.) and 10% FCS-containing RPMI1640, respectively. Each test agent was added to HUVEC upon the addition of IL-1β or TNFα and to U937 24 hours prior to the cell adhesion test. The inhibitory activity was calculated out according to the equation [100–(C–B)/(A–B)×100 (%)], wherein A is the number of U937 cells adhered to HUVEC stimulated by IL–1β or TNFα when no test agent was added, B is the number of U937 cells adhered to HUVEC not stimulated by IL–1β or TNFα when no test agent was added, and C is the number of U937 cells adhered to HUVEC stimulated by ILβ or TNFα when the test agent was added. The results are shown in Table 1. As control compounds, Test Compound 1 described in Japanese Patent Application Laid-Open No. 9-143075 and dilazep described in Japanese Patent Application Laid-Open No. 11-92382 were simultaneously evaluated.

TABLE 1

Inhibitory activity of each compound at 1 μM against cell adhesion

| Example | Percent inhibition (%) | |
|---|---|---|
| | Stimulation by $TNF_\alpha$ | Stimulation by IL-1$_\beta$ |
| 4 | 43 | 42 |
| 9 | 64 | 53 |
| 10 | 71 | 63 |
| 22 | 50 | 34 |
| Test compound 1 | 5 | 10 |
| Dilazep | 12 | 0 |

Specific formulation examples will hereinafter be described.

PREPARATION EXAMPLE 62

Capsule Preparation

| | |
|---|---|
| N,N'-Bis[2-(3,4,5-trimethoxyphenyl)pyridin-4-yl)methyl]piperazine | 30 mg |
| Microcrystalline cellulose | 30 mg |
| Lactose | 30 mg |
| Magnesium stearate | 3 mg |
| Total amount | 93 mg. |

The above ingredients were mixed in accordance with a method known per se in the art and then charged in a gelatin capsule to obtain a capsule preparation.

PREPARATION EXAMPLE 63

Tablet Preparation

| | |
|---|---|
| N,N'-Bis[2-(3,4,5-trimethoxyphenyl)pyridin-4-yl)methyl]piperazine | 30 mg |
| Starch | 44 mg |
| Starch (for glue) | 5.6 mg |
| Magnesium stearate | 0.4 mg |
| Calcium carboxymethyl cellulose | 20 mg |
| Total amount | 100 mg. |

The above ingredients were mixed in accordance with a method known per se in the art to obtain a tablet preparation.

PREPARATION EXAMPLE 64

Injection Preparation

N,N'-Bis[2-(3,4,5-trimethoxyphenyl)pyridin-4-yl)methyl]piperazine (100 mg) and sodium chloride (900 mg) were dissolved in distilled water (about 80 mL) for injection, and distilled water for injection was added to the resultant solution to 100 mL in total. This diluted solution was sterilized by filtration and then subdivided and charged into 10 light-screening ampoules, and the ampoules were sealed to obtain injection preparations.

As described above, the compounds (1) according to the present invention have inhibitory effects on both cell adhesion and cell infiltration and are useful as agents for prevention or treatment of diseases such as allergy, asthma, rheumatism, arteriosclerosis and inflammation.

Obviously, numerous modifications of the above teachings are apparent to those skilled in the art. Therefore, within the scope of the appended claims the invention may be practiced otherwise than as specifically described herein.

What is claimed is:

1. A compound of formula (1):

(1)

[Chemical structure showing: MeO-substituted phenyl ring connected via A to a pyridine/pyrazine ring (with X and Y), then –(CH$_2$)$_n$–N, piperazine ring with (CH$_2$)$_m$, N–(CH$_2$)$_n$– connected to another trimethoxyphenyl group with OMe substituents]

wherein A is a single bond or C≡C; X and Y are individually CH or a nitrogen atom; m is 1 or 2; and n is a number of 1 to 5;

an acid-addition salt thereof, or a hydrate thereof.

2. A pharmaceutical composition comprising, as an active ingredient, a compound of formula (1):

(1)

[Chemical structure as above]

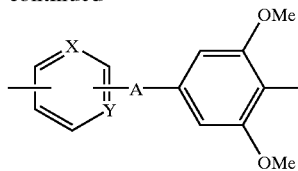

wherein A is a single bond or C≡C; X and Y are individually CH or a nitrogen atom; m is 1 or 2; and n is a number of 1 to 5;
an acid-addition salt thereof, or a hydrate thereof, and a pharmaceutically acceptable carrier.

3. The pharmaceutical composition of claim 2, comprising an effective amount of the compound of formula (1) for treating one or more diseases caused by cell adhesion and/or cell infiltration selected from the group consisting of allergy, asthma, inflammation, rheumatism and arteriosclerosis.

4. A method for treating one or more diseases caused by cell adhesion and/or cell infiltration selected from the group consisting of allergy, asthma, inflammation, rheumatism and arteriosclerosis, which comprises administering to a patient in need thereof an effective amount of a compound of formula (1):

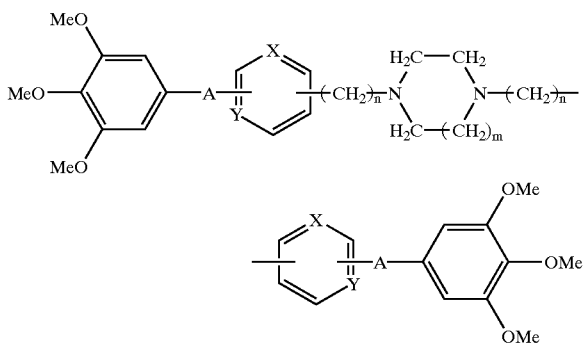

(1)

wherein A is a single bond or C≡C; X and Y are individually CH or a nitrogen atom; m is 1 or 2; and n is a number of 1 to 5;

an acid-addition salt thereof, or a hydrate thereof.

5. The compound of formula (1) of claim 1, wherein said compound of formula (1) is N,N'-bis[3-(3,4,5-trimethoxyphenyl)benzyl]-homopiperazine.

6. The compound of formula (1) of claim 1, wherein said compound of formula (1) is N,N'-bis[[2-(3,4,5-trimethoxyphenyl)pyridin-4-yl]methyl]piperazine.

7. The compound of formula (1) of claim 1, wherein said compound of formula (1) is N,N'-bis[[2-(3,4,5-trimethoxyphenyl)pyridin-4-yl]methyl]homopiperazine.

8. The compound of formula (1) of claim 1, wherein said compound of formula (1) is N,N'-bis[[2-(3,4,5-trimethoxyphenylethynyl)-pyridin-4-yl]methyl]piperazine.

9. The pharmaceutical composition of claim 2, wherein said compound of formula (1) is N,N'-bis[3-(3,4,5-trimethoxyphenyl)benzyl]-homopiperazine.

10. The pharmaceutical composition of claim 2, wherein said compound of formula (1) is N,N'-bis[[2-(3,4,5-trimethoxyphenyl)pyridin-4-yl]methyl]piperazine.

11. The pharmaceutical composition of claim 2, wherein said compound of formula (1) is N,N'-bis[[2-(3,4,5-trimethoxyphenyl)pyridin-4-yl]methyl]homopiperazine.

12. The pharmaceutical composition of claim 2, wherein said compound of formula (1) is N,N'-bis[[2-(3,4,5-trimethoxyphenylethynyl)-pyridin-4-yl]methyl]piperazine.

13. The method of claim 4, wherein the compound of formula (1) is admixed with a pharmaceutically acceptable carrier.

14. The method of claim 4, wherein said compound of formula (1) is N,N'-bis[3-(3,4,5-trimethoxyphenyl)benzyl]-homopiperazine.

15. The method of claim 4, wherein said compound of formula (1) is N,N'-bis[[2-(3,4,5-trimethoxyphenyl)pyridin-4-yl]methyl]piperazine.

16. The method of claim 4, wherein said compound of formula (1) is N,N'-bis[[2-(3,4,5-trimethoxyphenyl)pyridin-4-yl]methyl]homopiperazine.

17. The method of claim 4, wherein said compound of formula (1) is N,N'-bis[[2-(3,4,5-trimethoxyphenylethynyl)-pyridin-4-yl]methyl]piperazine.

* * * * *